(12) United States Patent
Ramaswamy et al.

(10) Patent No.: US 8,535,925 B2
(45) Date of Patent: Sep. 17, 2013

(54) MODIFIED DNASE COMPOSITIONS AND METHODS OF USE THEREOF

(75) Inventors: Gayathri Ramaswamy, Union City, CA (US); Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 542 days.

(21) Appl. No.: 12/753,444

(22) Filed: Apr. 2, 2010

(65) Prior Publication Data

US 2012/0225467 A1 Sep. 6, 2012

Related U.S. Application Data

(60) Provisional application No. 61/168,490, filed on Apr. 10, 2009.

(51) Int. Cl.
*C12N 9/16* (2006.01)

(52) U.S. Cl.
USPC ........ 435/196; 435/199; 536/23.2; 424/94.61

(58) Field of Classification Search
None
See application file for complete search history.

(56) References Cited

U.S. PATENT DOCUMENTS

| | | | |
|---|---|---|---|
| 7,067,298 B2 | 6/2006 | Latham et al. | |
| 7,670,808 B2 | 3/2010 | Wang et al. | |
| 2002/0173025 A1 | 11/2002 | Lazarus et al. | |
| 2004/0081963 A1 | 4/2004 | Wang | |
| 2004/0219529 A1 | 11/2004 | Latham et al. | |

FOREIGN PATENT DOCUMENTS

| | | |
|---|---|---|
| EP | 1 832 652 A2 | 9/2007 |
| WO | WO 97/47751 A1 | 12/1997 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
The Supplementary European Search Report from EP 10762243.3, mailed Aug. 1, 2012.
Takeshita et al.; "Amphibian DNases I are characterized by a C-terminal end with a unique, cysteine-rich stretch and by the insertion of a serine residue into the Ca2+-binding site"; *Biochem. J.*; 357:473-480 (Jul 2001).
Database UniProt, Accession No. Q4AEE3, Equus caballus deoxyribonuclease I. Sep. 13, 2005.
Database UniProt, Accession No. P00639, Bos taurus deoxyribonuclease I. Jul. 21, 1986.
Jones, Stephen J. et al.; "Site-directed Mutagenesis of the Catalytic Residues of Bovine Pancreatic Deoxyribonuclease I"; 1996, *J. Mol. Biol.*, vol. 264, pp. 1154-1163.
Krough, Berit Olsen et al.; "A poxvirus-like type IB topoisomerase family in bacteria"; 2002, *PNAS*, vol. 99, No. 4, pp. 1853-1858.
Pan, Clark Q. et al.; "Hyperactivity of Human DNase I Varients"; 1998, *The Journal of Biological Chemistry*, vol. 273, No. 19, pp. 11701-11708.
Pan, Clark Q. et al.; "Mutational analysis of human DNase I at the DNA binding interface: Implications for DNA recognition catalysis, and metal ion dependence"; 1998, *Protein Science*, vol. 7, pp. 628-636.
Shehi, Erlet et al.; "Thermal Stability and DNA Binding Activity of a Variant Form of the Sso7d Protein from the Archeon *Sulfolobus solfataricus* Truncated at Leucine 54"; 2003, *Biochemistry*, vol. 42, pp. 8362-8368.
Suck, Dietrich et al.; "Three-dimensional structure of bovine pancreatic DNase I"; 1984, *The EMBO Journal*, vol. 3, No. 10, pp. 2423-2430.
Takeshita, Haruo et al.; "A single amino acid substitution of Leu130Ile in snake DNases I contributes to the acquisition of thermal stability"; 2003, *Eur. J. Biochem.*, vol. 270, pp. 307-314.

* cited by examiner

*Primary Examiner* — Richard Hutson
(74) *Attorney, Agent, or Firm* — Kilpatrick Townsend & Stockton LLP

(57) ABSTRACT

Modified DNase polypeptides and methods of their use are provided.

10 Claims, 6 Drawing Sheets

FIGURE 1

| | | | | | | | | | | 10 | | | | | | | | | | 20 | | | | | | | | | 30 | | | | | | | |
|---|---|---|---|---|---|---|---|---|---|---|---|---|---|---|---|---|---|---|---|---|---|---|---|---|---|---|---|---|---|---|---|---|---|---|---|---|
| Bovine | . | K | . | . | . | . | . | . | . | . | . | . | . | . | . | . | . | . | . | . | A | . | . | . | . | R | . | V | R | . | . | . | . | V | . | . |
| Human | . | K | . | . | . | . | . | Q | . | . | . | . | . | . | . | . | . | . | V | . | . | . | . | Q | . | . | . | . | . | . | . | . | . | V |
| Equine | . | . | . | . | . | . | . | . | . | . | . | . | . | . | . | D | . | . | . | N | . | . | . | Q | . | . | N | . | . | . | . | . | . |
| Ovine | . | K | . | . | . | . | . | . | . | . | . | . | . | . | . | . | . | . | . | . | . | . | . | . | R | . | . | R | . | . | . | . | . | . |
| Porcine | . | . | . | . | . | . | . | . | . | . | . | . | . | . | . | . | . | . | . | . | . | . | N | . | . | . | R | . | . | . | . | . | . | . |
| Canine | . | . | M | . | . | . | . | . | . | . | . | . | . | . | . | . | . | . | . | . | . | K | . | . | . | Q | . | . | . | . | . | V | . | V | V |
| Rabbit | . | K | . | . | . | . | . | . | S | . | . | . | . | . | . | . | . | . | . | . | . | T | . | . | . | . | R | . | . | Q | . | . | . | . | . |
| Mouse | . | . | . | . | . | . | . | . | . | . | . | . | . | . | . | . | . | . | . | . | V | . | F | . | K | . | . | . | . | . | . | . | . | V | . |
| Rat | . | . | . | . | . | . | . | . | . | . | D | . | . | . | . | . | . | . | . | . | . | . | . | . | K | . | . | . | . | . | . | . | . | V | V |
| | L | r | i | A | A | F | N | I | r | t | F | G | e | T | K | M | S | N | a | T | L | s | s | Y | i | V | X | I | l | s | R | Y | D | i | a | l | i |

| | | | | | | 40 | | | | | | | | | | 50 | | | | | | | | | 60 | | | | | | | | | 70 | | | | |
|---|---|---|---|---|---|---|---|---|---|---|---|---|---|---|---|---|---|---|---|---|---|---|---|---|---|---|---|---|---|---|---|---|---|---|---|---|---|
| Bovine | . | . | . | . | . | . | . | V | . | . | . | . | . | . | Y | . | . | . | . | . | . | . | . | . | . | . | . | . | . | . | . | . | . | . | . | . | N |
| Human | . | . | . | . | . | . | . | . | . | . | . | . | . | . | N | . | . | . | A | . | D | . | . | . | . | . | . | . | . | . | . | . | . | . | . | . | N |
| Equine | . | . | . | . | . | . | . | . | . | . | . | . | . | . | R | . | . | . | . | . | . | . | . | . | . | F | . | . | . | . | . | . | . | . | . | . | N |
| Ovine | . | . | . | . | . | . | V | . | . | . | . | . | . | . | D | . | . | . | . | . | . | . | S | . | . | . | . | . | . | . | . | . | . | . | . | . | N |
| Porcine | . | . | . | . | . | . | . | . | . | . | . | . | N | E | . | . | . | . | . | . | . | . | N | . | . | H | . | . | . | . | . | . | . | . | . | . | S |
| Canine | . | . | . | . | . | . | . | . | . | . | . | . | . | . | T | . | . | . | . | . | . | . | A | . | . | . | . | . | . | . | . | . | . | . | . | . | S |
| Rabbit | . | . | . | . | . | . | . | . | . | . | . | . | . | . | K | . | . | E | K | A | A | D | . | . | R | F | . | A | . | . | . | . | . | . | . | . | R |
| Mouse | . | . | . | . | . | . | V | . | . | . | . | . | . | . | E | . | . | R | . | K | . | D | . | . | R | . | . | . | . | . | . | . | . | . | . | . | K |
| Rat | . | . | . | . | T | . | . | V | . | . | . | . | . | . | E | . | . | R | . | I | . | D | N | . | R | . | I | I | . | . | . | . | . | . | . | . | K |
| | Q | E | V | R | D | s | H | L | t | A | V | G | K | L | L | d | X | L | N | q | d | d | p | n | t | Y | h | y | v | v | S | E | P | L | G | R | X |

| | | | | | | 80 | | | | | | | | | 90 | | | | | | | | | 100 | | | | | | | | | 110 | | | | |
|---|---|---|---|---|---|---|---|---|---|---|---|---|---|---|---|---|---|---|---|---|---|---|---|---|---|---|---|---|---|---|---|---|---|---|---|---|
| Bovine | . | . | . | . | . | . | . | L | . | . | . | N | K | . | . | . | . | T | . | . | . | . | . | . | . | S | . | . | . | . | S | . | . | . |
| Human | . | . | . | . | . | . | . | Y | . | . | . | . | . | A | V | . | . | . | Y | . | . | . | . | . | . | . | . | . | . | . | . | N | . |
| Equine | N | . | . | . | . | . | . | . | . | . | . | . | . | . | L | . | . | . | . | . | N | . | . | . | . | . | . | . | . | . | . | . | . |
| Ovine | . | . | . | . | . | . | . | . | . | N | K | . | . | . | . | T | . | . | . | . | . | . | . | S | . | . | . | . | S | . | . | . |
| Porcine | T | . | . | . | . | . | . | . | . | . | . | . | . | . | . | . | . | . | L | . | . | . | . | . | . | . | . | . | . | . | N | . |
| Canine | . | . | . | . | . | . | . | L | . | . | . | . | R | . | . | . | . | . | . | . | . | . | . | . | . | . | . | . | . | . | . | . |
| Rabbit | T | . | . | . | . | . | . | Y | . | . | . | . | . | . | . | . | . | . | Y | . | . | . | . | . | . | . | T | . | . | . | . | . |
| Mouse | . | . | . | . | Q | . | . | . | Y | . | . | . | . | . | I | . | . | . | . | . | . | . | . | . | . | . | . | . | . | . | . | . | . |
| Rat | . | . | . | . | Q | . | . | Y | . | . | S | . | . | . | . | . | . | . | H | . | . | . | . | . | . | . | . | . | . | . | . | . |
| | s | Y | K | E | r | Y | L | F | v | f | R | P | d | q | V | S | v | l | D | s | Y | q | Y | d | D | G | C | E | p | C | G | n | D | t | F | s | R |

|  | | | | | | 230 | | | | | | | | | | | 240 | | | | | | | | | | 250 | | | | | | | | | |
|---|---|---|---|---|---|---|---|---|---|---|---|---|---|---|---|---|---|---|---|---|---|---|---|---|---|---|---|---|---|---|---|---|---|---|---|---|
| Bovine | S | S | . | . | . | G | . | . | A | . | . | . | . | . | . | . | . | . | . | . | E | M | . | L | . | . | . | . | . | . | . | . | . | . | . | . |
| Human | G | . | . | . | . | D | . | . | L | . | . | N | . | . | . | . | . | . | . | D | . | L | . | Q | . | . | . | . | . | . | . | . | . | . | M | . |
| Equine | E | . | . | . | . | D | . | . | V | . | . | . | . | . | . | . | . | N | D | . | T | . | E | . | . | . | . | . | . | . | . | . | . | . | . | . |
| Ovine | S | S | . | . | . | G | . | . | V | . | . | . | . | . | . | . | . | . | . | . | E | M | . | L | . | . | . | . | . | . | . | . | . | . | . | . |
| Porcine | R | . | . | . | . | D | . | . | A | . | . | . | . | . | F | . | . | . | E | . | T | . | L | . | . | . | . | . | . | . | . | . | . | . | . | . |
| Canine | H | . | . | . | . | E | . | . | A | . | . | N | . | . | V | . | . | . | S | . | L | . | Q | . | . | . | . | . | . | . | . | . | . | . | . | . |
| Rabbit | D | . | . | . | . | N | . | . | A | . | . | N | . | . | . | . | . | . | . | . | L | . | Q | . | . | . | . | . | . | . | . | . | . | . | . | . |
| Mouse | A | . | . | . | . | N | . | . | V | . | . | . | . | . | E | . | . | . | . | . | L | . | E | . | . | . | . | . | . | . | . | . | . | . | . | . |
| Rat | A | . | . | . | . | S | . | . | V | . | . | . | . | . | E | . | R | . | T | . | . | M | . | E | . | . | . | . | . | . | . | . | . | . | . | . |
|  | X | a | V | V | P | X | S | A | X | P | F | d | F | Q | a | a | y | g | L | s | n | q | X | A | X | A | I | S | D | H | Y | P | V | E | V | t | L |

|  | 260 | | |
|---|---|---|---|
| Bovine | T | – | – |
| Human | K | – | – |
| Equine | M | – | – |
| Ovine | T | – | – |
| Porcine | K | R | A |
| Canine | K | R | A |
| Rabbit | A | – | – |
| Mouse | R | L | I |
| Rat | R | K | T |
|  | X | X | X |

SEQUENCE LISTING

```
<160> NUMBER OF SEQ ID NOS: 29

<210> SEQ ID NO 1
<211> LENGTH: 15
<212> TYPE: PRT
<213> ORGANISM: Artificial Sequence
<220> FEATURE:
<223> OTHER INFORMATION: synthetic DNase I motif with positively-charged
      basic amino acids at positions Q9 and E13
      conferring hyperactivity
<220> FEATURE:
<221> NAME/KEY: VARIANT
<222> LOCATION: (6)...(6)
<223> OTHER INFORMATION: Xaa = basic amino acid (His, Arg, Lys, Asn or
      Gln)
<220> FEATURE:
<221> NAME/KEY: VARIANT
<222> LOCATION: (7)...(7)
<223> OTHER INFORMATION: Xaa = Ser or Thr
<220> FEATURE:
<221> NAME/KEY: VARIANT
<222> LOCATION: (10)...(10)
<223> OTHER INFORMATION: Xaa = basic amino acid (His, Arg, Lys, Asn or
      Gln)

<400> SEQUENCE: 1

Ala Ala Phe Asn Ile Xaa Xaa Phe Gly Xaa Thr Lys Met Ser Asn
 1               5                  10                  15

<210> SEQ ID NO 2
<211> LENGTH: 11
<212> TYPE: PRT
<213> ORGANISM: Artificial Sequence
<220> FEATURE:
<223> OTHER INFORMATION: synthetic DNase I motif with positively-charged
      basic amino acid at position N74 conferring heat
      lability
<220> FEATURE:
<221> NAME/KEY: VARIANT
<222> LOCATION: (7)...(7)
<223> OTHER INFORMATION: Xaa = basic amino acid (His, Arg, Lys, Asn or
      Gln)
<220> FEATURE:
<221> NAME/KEY: VARIANT
<222> LOCATION: (8)...(8)
```

-continued

<223> OTHER INFORMATION: Xaa = Ser, Thr or Asn

<400> SEQUENCE: 2

Ser Glu Pro Leu Gly Arg Xaa Xaa Tyr Lys Glu
 1               5                  10

<210> SEQ ID NO 3
<211> LENGTH: 7
<212> TYPE: PRT
<213> ORGANISM: Artificial Sequence
<220> FEATURE:
<223> OTHER INFORMATION: synthetic DNase I motif with Leu130 conferring
      heat lability
<220> FEATURE:
<221> NAME/KEY: VARIANT
<222> LOCATION: (5)...(5)
<223> OTHER INFORMATION: Xaa = Ala or Pro

<400> SEQUENCE: 3

Phe Ala Leu Val Xaa Leu His
 1               5

<210> SEQ ID NO 4
<211> LENGTH: 20
<212> TYPE: PRT
<213> ORGANISM: Artificial Sequence
<220> FEATURE:
<223> OTHER INFORMATION: synthetic DNase I motif with Ser-205 conferring
      heat lability
<220> FEATURE:
<221> NAME/KEY: VARIANT
<222> LOCATION: (5)...(5)
<223> OTHER INFORMATION: Xaa = Ala, Ser or Val
<220> FEATURE:
<221> NAME/KEY: VARIANT
<222> LOCATION: (7)...(7)
<223> OTHER INFORMATION: Xaa = Thr, Ser or Lys
<220> FEATURE:
<221> NAME/KEY: VARIANT
<222> LOCATION: (8)...(8)
<223> OTHER INFORMATION: Xaa = Ser or Pro
<220> FEATURE:
<221> NAME/KEY: VARIANT
<222> LOCATION: (10)...(10)
<223> OTHER INFORMATION: Xaa = Asn or His

<400> SEQUENCE: 4

Ala Asp Thr Thr Xaa Ser Xaa Xaa Thr Xaa Cys Ala Tyr Asp Arg Ile
 1               5                  10                  15

Val Val Ala Gly
            20

<210> SEQ ID NO 5
<211> LENGTH: 260
<212> TYPE: PRT
<213> ORGANISM: Homo sapiens
<220> FEATURE:
<223> OTHER INFORMATION: human DNase I (phosphodiesterase)

<400> SEQUENCE: 5

Leu Lys Ile Ala Ala Phe Asn Ile Gln Thr Phe Gly Glu Thr Lys Met
 1               5                  10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

```
Tyr Val Val Ser Glu Pro Leu Gly Arg Asn Ser Tyr Lys Glu Arg Tyr
 65                  70                  75                  80

Leu Phe Val Tyr Arg Pro Asp Gln Val Ser Ala Val Asp Ser Tyr Tyr
                 85                  90                  95

Tyr Asp Asp Gly Cys Glu Pro Cys Gly Asn Asp Thr Phe Asn Arg Glu
                100                 105                 110

Pro Ala Ile Val Arg Phe Phe Ser Arg Phe Thr Glu Val Arg Glu Phe
            115                 120                 125

Ala Ile Val Pro Leu His Ala Ala Pro Gly Asp Ala Val Ala Glu Ile
            130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Thr Pro Thr His
            195                 200                 205

Cys Ala Tyr Asp Arg Ile Val Val Ala Gly Met Leu Leu Arg Gly Ala
210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 6
<211> LENGTH: 260
<212> TYPE: PRT
<213> ORGANISM: Bos taurus
<220> FEATURE:
<223> OTHER INFORMATION: bovine DNase I (phosphodiesterase)

<400> SEQUENCE: 6

Leu Lys Ile Ala Ala Phe Asn Ile Arg Thr Phe Gly Glu Thr Lys Met
 1               5                  10                  15

Ser Asn Ala Thr Leu Ala Ser Tyr Ile Val Arg Ile Val Arg Arg Tyr
                20                  25                  30

Asp Ile Val Leu Ile Gln Glu Val Arg Asp Ser His Leu Val Ala Val
            35                  40                  45

Gly Lys Leu Leu Asp Tyr Leu Asn Gln Asp Asp Pro Asn Thr Tyr His
 50                  55                  60

Tyr Val Val Ser Glu Pro Leu Gly Arg Asn Ser Tyr Lys Glu Arg Tyr
 65                  70                  75                  80

Leu Phe Leu Phe Arg Pro Asn Lys Val Ser Val Leu Asp Thr Tyr Gln
                 85                  90                  95

Tyr Asp Asp Gly Cys Glu Ser Cys Gly Asn Asp Ser Phe Ser Arg Glu
                100                 105                 110

Pro Ala Val Val Lys Phe Ser Ser His Ser Thr Lys Val Lys Glu Phe
            115                 120                 125

Ala Ile Val Ala Leu His Ser Ala Pro Ser Asp Ala Val Ala Glu Ile
            130                 135                 140

Asn Ser Leu Tyr Asp Val Tyr Leu Asp Val Gln Gln Lys Trp His Leu
145                 150                 155                 160

Asn Asp Val Met Leu Met Gly Asp Phe Asn Ala Asp Cys Ser Tyr Val
```

-continued

```
                  165                 170                 175
Thr Ser Ser Gln Trp Ser Ser Ile Arg Leu Arg Thr Ser Ser Thr Phe
                180                 185                 190

Gln Trp Leu Ile Pro Asp Ser Ala Asp Thr Thr Ala Thr Ser Thr Asn
            195                 200                 205

Cys Ala Tyr Asp Arg Ile Val Val Ala Gly Ser Leu Leu Gln Ser Ser
210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260

<210> SEQ ID NO 7
<211> LENGTH: 260
<212> TYPE: PRT
<213> ORGANISM: Ovis aries
<220> FEATURE:
<223> OTHER INFORMATION: ovine DNase I (phosphodiesterase)

<400> SEQUENCE: 7

Leu Lys Ile Ala Ala Phe Asn Ile Arg Thr Phe Gly Glu Thr Lys Met
1               5                   10                  15

Ser Asn Ala Thr Leu Ser Ser Tyr Ile Val Arg Ile Leu Arg Arg Tyr
                20                  25                  30

Asp Ile Ala Leu Ile Gln Glu Val Arg Asp Ser His Leu Val Ala Val
            35                  40                  45

Gly Lys Leu Leu Asp Asp Leu Asn Gln Asp Asp Pro Asn Ser Tyr His
50                  55                  60

Tyr Val Val Ser Glu Pro Leu Gly Arg Asn Ser Tyr Lys Glu Arg Tyr
65                  70                  75                  80

Leu Phe Val Phe Arg Pro Asn Lys Val Ser Val Leu Asp Thr Tyr Gln
                85                  90                  95

Tyr Asp Asp Gly Cys Glu Ser Cys Gly Asn Asp Ser Phe Ser Arg Glu
            100                 105                 110

Pro Ala Val Val Lys Phe Ser Ser Pro Ser Thr Lys Val Lys Ala Phe
            115                 120                 125

Ala Ile Val Pro Leu His Ser Ala Pro Ser Asp Ala Val Ala Glu Ile
130                 135                 140

Asn Ser Leu Tyr Asp Val Tyr Leu Asp Val Gln Gln Lys Trp Asp Leu
145                 150                 155                 160

Asn Asp Ile Met Leu Met Gly Asp Phe Asn Ala Asp Cys Ser Tyr Val
                165                 170                 175

Thr Ser Ser Gln Trp Ser Ser Ile Arg Leu Arg Thr Ser Ser Thr Phe
                180                 185                 190

Gln Trp Leu Ile Pro Asp Ser Ala Asp Thr Thr Ala Thr Ser Thr Asn
            195                 200                 205

Cys Ala Tyr Asp Arg Ile Val Val Ala Gly Ser Leu Leu Gln Ser Ser
210                 215                 220

Val Val Pro Gly Ser Ala Val Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260
```

<210> SEQ ID NO 8
<211> LENGTH: 260
<212> TYPE: PRT
<213> ORGANISM: Equus caballus
<220> FEATURE:
<223> OTHER INFORMATION: equine DNase I (phosphodiesterase)

<400> SEQUENCE: 8

Leu Arg Ile Ala Ala Phe Asn Ile Arg Thr Phe Gly Glu Thr Lys Met
 1               5                  10                  15

Ser Asn Asp Thr Leu Ser Asn Tyr Ile Val Gln Ile Leu Asn Arg Tyr
            20                  25                  30

Asp Ile Ala Leu Ile Gln Glu Val Arg Asp Ser His Leu Thr Ala Val
        35                  40                  45

Gly Lys Leu Leu Asp Arg Leu Asn Gln Asp Pro Asn Thr Tyr His
    50                  55                  60

Phe Val Val Ser Glu Pro Leu Gly Arg Asn Asn Tyr Lys Glu Arg Tyr
65                  70                  75                  80

Leu Phe Val Phe Arg Pro Asp Gln Val Ser Leu Leu Asp Ser Tyr Gln
                85                  90                  95

Tyr Asn Asp Gly Cys Glu Pro Cys Gly Asn Asp Thr Phe Ser Arg Glu
            100                 105                 110

Pro Ala Ile Val Lys Phe Ser Ser Pro Phe Thr Gln Val Lys Glu Phe
        115                 120                 125

Ala Ile Val Pro Leu His Ala Ala Pro Ser Asp Ala Leu Ala Glu Ile
    130                 135                 140

Asp Ser Leu Tyr Asp Val Tyr Leu Asp Val Gln Gln Lys Trp Asp Met
145                 150                 155                 160

Glu Asp Ile Met Leu Met Gly Asp Phe Asn Ala Gly Cys Ser Tyr Val
                165                 170                 175

Thr Ser Ser Gln Trp Pro Ser Ile Arg Leu Arg Arg Asn Pro Ala Phe
            180                 185                 190

Trp Trp Leu Ile Pro Asp Thr Ala Asp Thr Thr Val Lys Ser Thr His
        195                 200                 205

Cys Ala Tyr Asp Arg Ile Val Val Ala Gly Thr Leu Leu Gln Glu Ala
    210                 215                 220

Val Val Pro Asp Ser Ala Val Pro Phe Asp Phe Gln Ala Ala Tyr Gly
225                 230                 235                 240

Leu Asn Asp Gln Thr Ala Glu Ala Ile Ser Asp His Tyr Pro Val Glu
                245                 250                 255

Val Thr Leu Met
            260

<210> SEQ ID NO 9
<211> LENGTH: 262
<212> TYPE: PRT
<213> ORGANISM: Canis familiaris
<220> FEATURE:
<223> OTHER INFORMATION: canine DNase I (phosphodiesterase)

<400> SEQUENCE: 9

Leu Arg Met Ala Ala Phe Asn Ile Arg Thr Phe Gly Glu Thr Lys Met
 1               5                  10                  15

Ser Asn Ala Thr Leu Ser Lys Tyr Ile Val Gln Ile Leu Ser Arg Tyr
            20                  25                  30

Asp Val Ala Val Val Gln Glu Val Arg Asp Ser His Leu Thr Ala Val
        35                  40                  45

```
Gly Lys Leu Leu Asp Thr Leu Asn Gln Asp Pro Asn Ala Tyr His
    50                  55                  60

Tyr Val Val Ser Glu Pro Leu Gly Arg Ser Ser Tyr Lys Glu Arg Tyr
 65              70                  75                  80

Leu Phe Leu Phe Arg Pro Asp Arg Val Ser Val Leu Asp Ser Tyr Gln
                85                  90                  95

Tyr Asp Asp Gly Cys Glu Pro Cys Gly Asn Asp Thr Phe Ser Arg Glu
            100                 105                 110

Pro Ala Ile Val Arg Phe His Ser Pro Leu Thr Glu Val Lys Glu Phe
            115                 120                 125

Ala Val Val Pro Leu His Ala Ala Pro Leu Asp Ala Val Ala Glu Ile
            130                 135                 140

Asp Ala Leu Tyr Asp Val Tyr Leu Asp Val Gln His Lys Trp Asp Leu
145                 150                 155                 160

Glu Asp Ile Val Leu Met Gly Asp Phe Asn Ala Gly Cys Ser Tyr Val
                165                 170                 175

Ala Ala Ser Gln Trp Ser Ser Ile Arg Leu Arg Thr Asn Pro Ala Phe
            180                 185                 190

Gln Trp Leu Ile Pro Asp Thr Ala Asp Thr Thr Ser Thr Ser Thr His
            195                 200                 205

Cys Ala Tyr Asp Arg Ile Val Val Ala Gly Ser Gln Leu Gln His Ala
210                 215                 220

Val Val Pro Glu Ser Ala Ala Pro Phe Asn Phe Gln Val Ala Tyr Gly
225                 230                 235                 240

Leu Ser Ser Gln Leu Ala Gln Ala Ile Ser Asp His Tyr Pro Val Glu
                245                 250                 255

Val Thr Leu Lys Arg Ala
            260

<210> SEQ ID NO 10
<211> LENGTH: 262
<212> TYPE: PRT
<213> ORGANISM: Sus scrofa
<220> FEATURE:
<223> OTHER INFORMATION: porcine DNase I (phosphodiesterase)

<400> SEQUENCE: 10

Leu Arg Ile Ala Ala Phe Asn Ile Arg Thr Phe Gly Glu Thr Lys Met
  1               5                  10                  15

Ser Asn Ala Thr Leu Ser Asn Tyr Ile Val Arg Ile Leu Ser Arg Tyr
             20                  25                  30

Asp Ile Ala Leu Ile Gln Glu Val Arg Asp Ser His Leu Thr Ala Val
         35                  40                  45

Gly Lys Leu Leu Asn Glu Leu Asn Gln Asp Pro Asn Asn Tyr His
    50                  55                  60

His Val Val Ser Glu Pro Leu Gly Arg Ser Thr Tyr Lys Glu Arg Tyr
 65              70                  75                  80

Leu Phe Val Phe Arg Pro Asp Gln Val Ser Val Leu Asp Ser Tyr Leu
                85                  90                  95

Tyr Asp Asp Gly Cys Glu Pro Cys Gly Asn Asp Thr Phe Asn Arg Glu
            100                 105                 110

Pro Ser Val Val Lys Phe Ser Ser Pro Ser Thr Gln Val Lys Glu Phe
            115                 120                 125

Ala Ile Val Pro Leu His Ala Ala Pro Ser Asp Ala Ala Ala Glu Ile
            130                 135                 140
```

```
Asp Ser Leu Tyr Asp Val Tyr Leu Asn Val Arg Gln Lys Trp Asp Leu
145                 150                 155                 160

Glu Asp Ile Met Leu Met Gly Asp Phe Asn Ala Gly Cys Ser Tyr Val
                165                 170                 175

Thr Thr Ser His Trp Ser Ser Ile Arg Leu Arg Glu Ser Pro Pro Phe
            180                 185                 190

Gln Trp Leu Ile Pro Asp Thr Ala Asp Thr Thr Val Ser Ser Thr His
        195                 200                 205

Cys Ala Tyr Asp Arg Ile Val Val Ala Gly Pro Leu Leu Gln Arg Ala
    210                 215                 220

Val Val Pro Asp Ser Ala Ala Pro Phe Asp Phe Gln Ala Ala Phe Gly
225                 230                 235                 240

Leu Ser Glu Gln Thr Ala Leu Ala Ile Ser Asp His Tyr Pro Val Glu
                245                 250                 255

Val Thr Leu Lys Arg Ala
            260

<210> SEQ ID NO 11
<211> LENGTH: 260
<212> TYPE: PRT
<213> ORGANISM: Oryctolagus cuniculus
<220> FEATURE:
<223> OTHER INFORMATION: rabbit DNase I (phosphodiesterase)

<400> SEQUENCE: 11

Leu Lys Ile Ala Ala Phe Asn Ile Arg Ser Phe Gly Glu Thr Lys Met
1               5                   10                  15

Ser Asn Ala Thr Leu Thr Ser Tyr Ile Val Arg Ile Leu Gln Arg Tyr
                20                  25                  30

Asp Ile Ala Leu Ile Gln Glu Val Arg Asp Ser His Leu Thr Ala Val
            35                  40                  45

Gly Lys Leu Leu Asp Lys Leu Asn Glu Lys Ala Ala Asp Thr Tyr Arg
    50                  55                  60

Phe Val Ala Ser Glu Pro Leu Gly Arg Arg Thr Tyr Lys Glu Arg Tyr
65                  70                  75                  80

Leu Phe Val Tyr Arg Pro Asp Gln Val Ser Val Leu Asp Ser Tyr Tyr
                85                  90                  95

Tyr Asp Asp Gly Cys Glu Pro Cys Gly Thr Asp Thr Phe Ser Arg Glu
                100                 105                 110

Pro Ala Val Val Arg Phe Ser Ser Pro Ser Thr Lys Val Arg Glu Phe
            115                 120                 125

Ala Ile Val Pro Leu His Ser Ala Pro Glu Asp Ala Val Ala Glu Ile
130                 135                 140

Asp Ala Leu Tyr Asp Val Tyr Leu Asp Val Gln Lys Lys Trp Gly Leu
145                 150                 155                 160

Gln Asp Val Met Leu Met Gly Asp Phe Asn Ala Asp Tyr Ser Tyr Val
                165                 170                 175

Thr Ser Ser Gln Trp Ser Ser Ile Arg Leu Arg Thr Asn Pro Ala Phe
            180                 185                 190

Lys Trp Leu Ile Pro Asp Thr Ala Asp Thr Thr Ala Thr Ser Thr Asn
        195                 200                 205

Cys Ala Tyr Asp Arg Ile Val Val Ala Gly Pro Leu Leu Gln Asp Ala
    210                 215                 220

Val Val Pro Asn Ser Ala Ala Pro Phe Asn Phe Gln Ala Ala Tyr Gly
225                 230                 235                 240

Leu Ser Asn Gln Leu Ala Gln Ala Ile Ser Asp His Tyr Pro Val Glu
```

```
                            245                 250                 255
Val Thr Leu Ala
            260

<210> SEQ ID NO 12
<211> LENGTH: 262
<212> TYPE: PRT
<213> ORGANISM: Mus musculus
<220> FEATURE:
<223> OTHER INFORMATION: mouse DNase I (phosphodiesterase)

<400> SEQUENCE: 12

Leu Arg Ile Ala Ala Phe Asn Ile Arg Thr Phe Gly Glu Thr Lys Met
 1               5                  10                  15

Ser Asn Ala Thr Leu Ser Val Tyr Phe Val Lys Ile Leu Ser Arg Tyr
            20                  25                  30

Asp Ile Ala Val Ile Gln Glu Val Arg Asp Ser His Leu Val Ala Val
        35                  40                  45

Gly Lys Leu Leu Asp Glu Leu Asn Arg Asp Lys Pro Asp Thr Tyr Arg
    50                  55                  60

Tyr Val Val Ser Glu Pro Leu Gly Arg Lys Ser Tyr Lys Glu Gln Tyr
65                  70                  75                  80

Leu Phe Val Tyr Arg Pro Asp Gln Val Ser Ile Leu Asp Ser Tyr Gln
                85                  90                  95

Tyr Asp Asp Gly Cys Glu Pro Cys Gly Asn Asp Thr Phe Ser Arg Glu
            100                 105                 110

Pro Ala Ile Val Lys Phe Phe Ser Pro Tyr Thr Glu Val Gln Glu Phe
        115                 120                 125

Ala Ile Val Pro Leu His Ala Ala Pro Thr Glu Ala Val Ser Glu Ile
    130                 135                 140

Asp Ala Leu Tyr Asp Val Tyr Leu Asp Val Trp Gln Lys Trp Gly Leu
145                 150                 155                 160

Glu Asp Ile Met Phe Met Gly Asp Phe Asn Ala Gly Cys Ser Tyr Val
                165                 170                 175

Thr Ser Ser Gln Trp Ser Ser Ile Arg Leu Arg Thr Ser Pro Ile Phe
            180                 185                 190

Gln Trp Leu Ile Pro Asp Ser Ala Asp Thr Thr Val Thr Ser Thr His
        195                 200                 205

Cys Ala Tyr Asp Arg Ile Val Val Ala Gly Ala Leu Leu Gln Ala Ala
    210                 215                 220

Val Val Pro Asn Ser Ala Val Pro Phe Asp Phe Gln Ala Glu Tyr Gly
225                 230                 235                 240

Leu Ser Asn Gln Leu Ala Glu Ala Ile Ser Asp His Tyr Pro Val Glu
                245                 250                 255

Val Thr Leu Arg Lys Ile
            260

<210> SEQ ID NO 13
<211> LENGTH: 262
<212> TYPE: PRT
<213> ORGANISM: Rattus norvegicus
<220> FEATURE:
<223> OTHER INFORMATION: rat DNase I (phosphodiesterase)

<400> SEQUENCE: 13

Leu Arg Ile Ala Ala Phe Asn Ile Arg Thr Phe Gly Asp Thr Lys Met
 1               5                  10                  15

Ser Asn Ala Thr Leu Ser Ser Tyr Ile Val Lys Ile Leu Ser Arg Tyr
```

```
                    20                  25                  30
Asp Ile Ala Val Val Gln Glu Val Arg Asp Thr His Leu Val Ala Val
                35                  40                  45
Gly Lys Leu Leu Asp Glu Leu Asn Arg Asp Ile Pro Asp Asn Tyr Arg
            50                  55                  60
Tyr Ile Ile Ser Glu Pro Leu Gly Arg Lys Ser Tyr Lys Glu Gln Tyr
65                  70                  75                  80
Leu Phe Val Tyr Arg Pro Ser Gln Val Ser Val Leu Asp Ser Tyr His
                85                  90                  95
Tyr Asp Asp Gly Cys Glu Pro Cys Gly Asn Asp Thr Phe Ser Arg Glu
                100                 105                 110
Pro Ala Ile Val Lys Phe Phe Ser Pro Tyr Thr Glu Val Arg Glu Phe
                115                 120                 125
Ala Ile Val Pro Leu His Ser Ala Pro Thr Glu Ala Val Ser Glu Ile
                130                 135                 140
Asp Ala Leu Tyr Asp Val Tyr Leu Asp Val Arg Gln Lys Trp Gly Leu
145                 150                 155                 160
Glu Asp Ile Met Phe Met Gly Asp Phe Asn Ala Gly Cys Ser Tyr Val
                165                 170                 175
Thr Ser Ser Gln Trp Ser Ser Ile Arg Leu Arg Thr Ser Pro Ile Phe
                180                 185                 190
Gln Trp Leu Ile Pro Asp Ser Ala Asp Thr Thr Ala Thr Ser Thr His
                195                 200                 205
Cys Ala Tyr Asp Arg Ile Val Val Ala Gly Ala Leu Leu Gln Ala Ala
                210                 215                 220
Val Val Pro Ser Ser Ala Val Pro Phe Asp Phe Gln Ala Glu Tyr Arg
225                 230                 235                 240
Leu Thr Asn Gln Met Ala Glu Ala Ile Ser Asp His Tyr Pro Val Glu
                245                 250                 255
Val Thr Leu Arg Lys Thr
                260

<210> SEQ ID NO 14
<211> LENGTH: 262
<212> TYPE: PRT
<213> ORGANISM: Gallus gallus
<220> FEATURE:
<223> OTHER INFORMATION: chicken DNase I (phosphodiesterase)

<400> SEQUENCE: 14

Leu Arg Ile Ser Ala Phe Asn Ile Arg Thr Phe Gly Asp Ser Lys Met
 1               5                  10                  15
Ser Asn Gln Thr Val Ala Gly Phe Ile Val Ser Ile Leu Val Gln Tyr
                20                  25                  30
Asp Ile Thr Leu Val Gln Glu Val Arg Asp Ala Asp Leu Ser Ser Val
                35                  40                  45
Lys Lys Leu Val Ser Gln Leu Asn Ser Ala Ser Ser Tyr Pro Tyr Ser
            50                  55                  60
Phe Leu Ser Ser Ile Pro Leu Gly Arg Asn Ser Tyr Lys Glu Gln Tyr
65                  70                  75                  80
Val Phe Ile Tyr Arg Ser Asp Ile Val Ser Val Leu Glu Ser Tyr Tyr
                85                  90                  95
Tyr Asp Asp Gly Cys Glu Ser Cys Gly Thr Asp Ile Phe Ser Arg Glu
                100                 105                 110
Pro Phe Ile Val Lys Phe Ser Ser Pro Thr Thr Gln Leu Asp Glu Phe
                115                 120                 125
```

```
Val Ile Val Pro Leu His Ala Glu Pro Ser Ser Ala Pro Ala Glu Ile
    130                 135                 140

Asn Ala Leu Thr Asp Val Tyr Thr Asp Val Ile Asn Lys Trp Glu Thr
145                 150                 155                 160

Asn Asn Ile Phe Phe Met Gly Asp Phe Asn Ala Asp Cys Ser Tyr Val
                165                 170                 175

Thr Ala Glu Gln Trp Pro Ser Ile Arg Leu Arg Ser Leu Ser Ser Cys
            180                 185                 190

Glu Trp Leu Ile Pro Asp Ser Ala Asp Thr Thr Val Thr Ser Thr Asp
        195                 200                 205

Cys Ala Tyr Asp Arg Ile Val Ala Cys Gly Ser Ala Leu Arg Gln Ala
    210                 215                 220

Val Glu Tyr Gly Ser Ala Thr Val Asn Asn Phe Gln Glu Thr Leu Arg
225                 230                 235                 240

Ile Gln Asn Lys Asp Ala Leu Ala Ile Ser Asp His Phe Pro Val Glu
                245                 250                 255

Val Thr Leu Lys Ala Arg
                260

<210> SEQ ID NO 15
<211> LENGTH: 262
<212> TYPE: PRT
<213> ORGANISM: Elaphe quadrivirgata
<220> FEATURE:
<223> OTHER INFORMATION: snake DNase I (phosphodiesterase)

<400> SEQUENCE: 15

Leu Arg Ile Gly Ala Phe Asn Ile Arg Ala Phe Gly Asp Lys Lys Leu
1               5                   10                  15

Ser Asn Gln Thr Ile Ser Ser Ile Val Arg Ile Leu Thr Thr Tyr
            20                  25                  30

Asp Leu Val Leu Ile Gln Glu Val Arg Asp Ala Asp Leu Ser Ala Val
        35                  40                  45

Lys Lys Leu Met Gln Leu Val Ser Gly Ala Ser Pro Asp Pro Phe Gly
50                  55                  60

Tyr Leu Ile Ser Lys Pro Leu Gly His Asn Ser Tyr Lys Glu Gln Tyr
65                  70                  75                  80

Leu Phe Val Tyr Arg Gln Asp Arg Val Ser Pro Val Glu Ser Tyr Tyr
                85                  90                  95

Tyr Asp Asp Gly Cys Glu Pro Cys Gly Asn Gly Thr Phe Ser Arg Glu
                100                 105                 110

Pro Phe Ile Val Lys Phe Ala Val Pro Gln Ala Ala Val Glu Glu Leu
            115                 120                 125

Val Leu Val Pro Leu His Ala Ala Pro Glu Ala Ala Val Thr Glu Ile
    130                 135                 140

Asp Ser Leu Tyr Asp Val Tyr Gln Asp Val Lys Asp Arg Trp Gly Val
145                 150                 155                 160

Thr Asp Ala Leu Leu Leu Gly Asp Phe Asn Ala Asp Cys Asn Tyr Val
                165                 170                 175

Gln Ala Glu Asp Trp Pro Ser Ile Arg Leu Arg Ser Ser Lys Asp Phe
            180                 185                 190

Gln Trp Leu Ile Pro Asp Thr Ala Asp Thr Thr Val Thr Asn Thr Ile
        195                 200                 205

Cys Ala Tyr Asp Arg Ile Val Ala Val Gly Ser Lys Leu Arg Glu Ser
    210                 215                 220
```

```
Ile Leu Pro Ala Thr Ala Lys Val Asp Asn Phe Gln Lys Thr Leu Lys
225                 230                 235                 240

Leu Ser Ser Lys Asp Ala Leu Ala Val Ser Asp His Phe Pro Val Glu
            245                 250                 255

Val Thr Leu Lys Ser Thr
            260

<210> SEQ ID NO 16
<211> LENGTH: 331
<212> TYPE: PRT
<213> ORGANISM: Xenopus laevis
<220> FEATURE:
<223> OTHER INFORMATION: African clawed frog DNase I (phosphodiesterase)

<400> SEQUENCE: 16

Phe Lys Ile Ala Ser Phe Asn Ile Gln Arg Phe Ser Met Thr Lys Val
1               5                   10                  15

Asp Asp Pro Val Val Leu Glu Leu Leu Ile Arg Ile Leu Ser Arg Tyr
            20                  25                  30

Glu Ile Ile Ala Ile Glu Glu Val Met Asn Ala Asp Asn Thr Ala Ile
        35                  40                  45

Ile Ser Leu Val Lys Glu Leu Ser Leu Ala Thr Lys Leu Asn Tyr Asn
50                  55                  60

Val Leu Ile Ser Asp His Leu Gly Arg Ser Ser Tyr Arg Glu Lys Tyr
65                  70                  75                  80

Ala Tyr Val Tyr Arg Glu Asp Ile Val Lys Pro Thr Glu Trp Tyr His
                85                  90                  95

Phe Asp Asp Gly Cys Glu Asn Cys Gly Thr Asp Ser Phe Ile Arg Glu
            100                 105                 110

Pro Phe Val Ala Arg Phe Thr Ser Leu Thr Thr Val Val Lys Asp Phe
        115                 120                 125

Ala Leu Ile Ser Ile His Thr Ser Pro Asp Tyr Ala Ile Met Glu Val
130                 135                 140

Asp Ala Leu Tyr Asp Ala Trp Val Asp Ala Lys Gln Arg Leu Lys Met
145                 150                 155                 160

Glu Asn Ile Leu Ile Leu Gly Asp Tyr Asn Ala Ala Cys Ser Tyr Val
                165                 170                 175

Ala Ser Arg His Trp Pro Ile Ile Arg Leu Arg His Val Glu Glu Leu
            180                 185                 190

Val Trp Leu Ile Gly Asp Lys Glu Asp Thr Thr Val Ser Thr Asn Thr
        195                 200                 205

Asn Cys Ala Tyr Asp Arg Met Val Ala Gly Gly Glu Glu Leu Gln Arg
210                 215                 220

Gly Ile Val Pro Asp Thr Ala Lys Ala Phe Asn Tyr His Val Ala Tyr
225                 230                 235                 240

Asp Leu Thr Tyr Glu Met Ala Lys Ala Val Ser Asp His Tyr Pro Val
                245                 250                 255

Glu Val Glu Leu Tyr Asp Asp Val Phe Tyr Ser Gly Gln Cys Phe Glu
            260                 265                 270

Pro Ser Ala Ser Thr Gly Ile Ser Gly Gly Leu Ser Leu Asn Gly Pro
        275                 280                 285

Cys Thr Cys Glu Gly Val Asp Phe Ser Ser Cys Arg Gly Arg Cys Gly
290                 295                 300

Ala Ser Gly Lys Thr Tyr Pro Cys Asn Cys Asn Ala Ser Cys Thr Asn
305                 310                 315                 320

Cys Cys Val Asp Tyr Thr Ser Ser Cys Lys Leu
```

<210> SEQ ID NO 17
<211> LENGTH: 262
<212> TYPE: PRT
<213> ORGANISM: Anguilla japonica
<220> FEATURE:
<223> OTHER INFORMATION: Japanese eel DNase I (phosphodiesterase)

<400> SEQUENCE: 17

Leu Phe Ile Gly Ala Phe Asn Ile Arg Ser Phe Gly Asp Lys Lys Ala
1               5                   10                  15

Ser Asn Ala Thr Leu Val Asp Ile Ile Val Lys Ile Val His Met Tyr
            20                  25                  30

Asp Ile Leu Leu Ile Gln Glu Val Arg Asp Ser Asp Leu Ser Ala Thr
        35                  40                  45

Lys Lys Leu Met Gln Asn Val Asn Gly Gly Ser Ser Pro His Lys Tyr
    50                  55                  60

Lys Tyr Ile Val Ser Glu Pro Leu Gly Arg Asn Thr Tyr Gln Glu Arg
65                  70                  75                  80

Tyr Leu Tyr Leu Tyr Arg Glu Asp Ser Val Ser Val Lys Asn Phe
                85                  90                  95

Thr Tyr Asp Asp Gly Ala Glu Ala Ser Gly Thr Asp Thr Phe Asn Arg
            100                 105                 110

Glu Pro Phe Val Val Met Phe Ser Ser Pro His Thr Arg Val Pro Glu
        115                 120                 125

Phe Ala Leu Val Pro Gln His Thr Ser Pro Asp Glu Ala Val Lys Glu
    130                 135                 140

Ile Asp Ala Leu Tyr Asp Val Ile Val Asp Ile Arg Ala Arg Trp Asn
145                 150                 155                 160

Thr Asp Asn Ile Ile Leu Leu Gly Asp Phe Asn Ala Gly Cys Asn Tyr
                165                 170                 175

Val Ala Gly Ser Asp Trp Gln Gln Ile Arg Leu Tyr Thr Asp Lys Ser
            180                 185                 190

Phe His Trp Leu Ile Pro Asp Ser Ala Asp Thr Thr Val Ser His Thr
        195                 200                 205

Asn Cys Pro Tyr Asp Arg Ile Val Ala Thr Thr Thr Met Met Glu Ala
    210                 215                 220

Val Val Pro His Ser Ala Ser Val Tyr Asp Tyr Met Thr Ser Leu Lys
225                 230                 235                 240

Leu Lys Leu Asp Met Ala Leu Ala Val Ser Asp His Phe Pro Val Glu
                245                 250                 255

Val Gln Leu Phe Gly Pro
            260

<210> SEQ ID NO 18
<211> LENGTH: 261
<212> TYPE: PRT
<213> ORGANISM: Artificial Sequence
<220> FEATURE:
<223> OTHER INFORMATION: synthetic equine DNase I "KS" mutant having two
      hyperactive (R13, K74) and two heat-labile (L130,
      S-205 insertion) mutations

<400> SEQUENCE: 18

Leu Arg Ile Ala Ala Phe Asn Ile Arg Thr Phe Gly Arg Thr Lys Met
1               5                   10                  15

Ser Asn Asp Thr Leu Ser Asn Tyr Ile Val Gln Ile Leu Asn Arg Tyr
            20                  25                  30

Asp Ile Ala Leu Ile Gln Glu Val Arg Asp Ser His Leu Thr Ala Val
             35                  40                  45

Gly Lys Leu Leu Asp Arg Leu Asn Gln Asp Asp Pro Asn Thr Tyr His
 50                  55                  60

Phe Val Val Ser Glu Pro Leu Gly Arg Lys Asn Tyr Lys Glu Arg Tyr
 65                  70                  75                  80

Leu Phe Val Phe Arg Pro Asp Gln Val Ser Leu Leu Asp Ser Tyr Gln
                 85                  90                  95

Tyr Asn Asp Gly Cys Glu Pro Cys Gly Asn Asp Thr Phe Ser Arg Glu
             100                 105                 110

Pro Ala Ile Val Lys Phe Ser Ser Pro Phe Thr Gln Val Lys Glu Phe
             115                 120                 125

Ala Leu Val Pro Leu His Ala Ala Pro Ser Asp Ala Leu Ala Glu Ile
         130                 135                 140

Asp Ser Leu Tyr Asp Val Tyr Leu Asp Val Gln Gln Lys Trp Asp Met
145                 150                 155                 160

Glu Asp Ile Met Leu Met Gly Asp Phe Asn Ala Gly Cys Ser Tyr Val
                 165                 170                 175

Thr Ser Ser Gln Trp Pro Ser Ile Arg Leu Arg Arg Asn Pro Ala Phe
             180                 185                 190

Trp Trp Leu Ile Pro Asp Thr Ala Asp Thr Thr Val Ser Lys Ser Thr
         195                 200                 205

His Cys Ala Tyr Asp Arg Ile Val Val Ala Gly Thr Leu Leu Gln Glu
         210                 215                 220

Ala Val Val Pro Asp Ser Ala Val Pro Phe Asp Phe Gln Ala Ala Tyr
225                 230                 235                 240

Gly Leu Asn Asp Gln Thr Ala Glu Ala Ile Ser Asp His Tyr Pro Val
                 245                 250                 255

Glu Val Thr Leu Met
             260

<210> SEQ ID NO 19
<211> LENGTH: 260
<212> TYPE: PRT
<213> ORGANISM: Artificial Sequence
<220> FEATURE:
<223> OTHER INFORMATION: synthetic equine DNase I "K" mutant having two
      hyperactive (R13, K74) and one heat-labile (L130)
      mutation

<400> SEQUENCE: 19

Leu Arg Ile Ala Ala Phe Asn Ile Arg Thr Phe Gly Arg Thr Lys Met
 1               5                  10                  15

Ser Asn Asp Thr Leu Ser Asn Tyr Ile Val Gln Ile Leu Asn Arg Tyr
             20                  25                  30

Asp Ile Ala Leu Ile Gln Glu Val Arg Asp Ser His Leu Thr Ala Val
             35                  40                  45

Gly Lys Leu Leu Asp Arg Leu Asn Gln Asp Asp Pro Asn Thr Tyr His
 50                  55                  60

Phe Val Val Ser Glu Pro Leu Gly Arg Lys Asn Tyr Lys Glu Arg Tyr
 65                  70                  75                  80

Leu Phe Val Phe Arg Pro Asp Gln Val Ser Leu Leu Asp Ser Tyr Gln
                 85                  90                  95

Tyr Asn Asp Gly Cys Glu Pro Cys Gly Asn Asp Thr Phe Ser Arg Glu
             100                 105                 110

Pro Ala Ile Val Lys Phe Ser Ser Pro Phe Thr Gln Val Lys Glu Phe

```
                115                 120                 125
Ala Leu Val Pro Leu His Ala Ala Pro Ser Asp Ala Leu Ala Glu Ile
130                 135                 140

Asp Ser Leu Tyr Asp Val Tyr Leu Asp Val Gln Gln Lys Trp Asp Met
145                 150                 155                 160

Glu Asp Ile Met Leu Met Gly Asp Phe Asn Ala Gly Cys Ser Tyr Val
                165                 170                 175

Thr Ser Ser Gln Trp Pro Ser Ile Arg Leu Arg Arg Asn Pro Ala Phe
            180                 185                 190

Trp Trp Leu Ile Pro Asp Thr Ala Asp Thr Thr Val Lys Ser Thr His
            195                 200                 205

Cys Ala Tyr Asp Arg Ile Val Val Ala Gly Thr Leu Leu Gln Glu Ala
210                 215                 220

Val Val Pro Asp Ser Ala Val Pro Phe Asp Phe Gln Ala Ala Tyr Gly
225                 230                 235                 240

Leu Asn Asp Gln Thr Ala Glu Ala Ile Ser Asp His Tyr Pro Val Glu
                245                 250                 255

Val Thr Leu Met
            260

<210> SEQ ID NO 20
<211> LENGTH: 15
<212> TYPE: PRT
<213> ORGANISM: Artificial Sequence
<220> FEATURE:
<223> OTHER INFORMATION: synthetic DNase I motif with positively-charged
      basic amino acids at positions Q9 and E13
      conferring hyperactivity
<220> FEATURE:
<221> NAME/KEY: VARIANT
<222> LOCATION: (7)...(7)
<223> OTHER INFORMATION: Xaa = Ser or Thr

<400> SEQUENCE: 20

Ala Ala Phe Asn Ile Arg Xaa Phe Gly Arg Thr Lys Met Ser Asn
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: synthetic DNase I motif with positively-charged
      basic amino acid at position N74 conferring heat
      lability
<220> FEATURE:
<221> NAME/KEY: VARIANT
<222> LOCATION: (8)...(8)
<223> OTHER INFORMATION: Xaa = Ser, Thr or Asn

<400> SEQUENCE: 21

Ser Glu Pro Leu Gly Arg Lys Xaa Tyr Lys Glu
1               5                   10

<210> SEQ ID NO 22
<211> LENGTH: 262
<212> TYPE: PRT
<213> ORGANISM: Artificial Sequence
<220> FEATURE:
<223> OTHER INFORMATION: synthetic DNase I consensus sequence
<220> FEATURE:
<221> NAME/KEY: VARIANT
<222> LOCATION: (27)...(262)
<223> OTHER INFORMATION: Xaa = any amino acid

<400> SEQUENCE: 22
```

```
Leu Arg Ile Ala Ala Phe Asn Ile Arg Thr Phe Gly Glu Thr Lys Met
 1               5                   10                  15

Ser Asn Ala Thr Leu Ser Ser Tyr Ile Val Xaa Ile Leu Ser Arg Tyr
            20                  25                  30

Asp Ile Ala Leu Ile Gln Glu Val Arg Asp Ser His Leu Thr Ala Val
            35                  40                  45

Gly Lys Leu Leu Asp Xaa Leu Asn Gln Asp Asp Pro Asn Thr Tyr His
        50                  55                  60

Tyr Val Val Ser Glu Pro Leu Gly Arg Xaa Ser Tyr Lys Glu Arg Tyr
65                  70                  75                  80

Leu Phe Val Phe Arg Pro Asp Gln Val Ser Val Leu Asp Ser Tyr Gln
                85                  90                  95

Tyr Asp Asp Gly Cys Glu Pro Cys Gly Asn Asp Thr Phe Ser Arg Glu
                100                 105                 110

Pro Ala Ile Val Lys Phe Ser Ser Pro Xaa Thr Xaa Val Lys Glu Phe
            115                 120                 125

Ala Ile Val Pro Leu His Ala Ala Pro Xaa Asp Ala Val Ala Glu Ile
        130                 135                 140

Asp Ala Leu Tyr Asp Val Tyr Leu Asp Val Gln Gln Lys Trp Xaa Leu
145                 150                 155                 160

Glu Asp Ile Met Leu Met Gly Asp Phe Asn Ala Gly Cys Ser Tyr Val
                165                 170                 175

Thr Ser Ser Gln Trp Ser Ser Ile Arg Leu Arg Thr Ser Pro Xaa Phe
            180                 185                 190

Gln Trp Leu Ile Pro Asp Ser Ala Asp Thr Thr Ala Thr Ser Thr His
        195                 200                 205

Cys Ala Tyr Asp Arg Ile Val Val Ala Gly Xaa Leu Leu Gln Xaa Ala
210                 215                 220

Val Val Pro Xaa Ser Ala Xaa Pro Phe Asp Phe Gln Ala Ala Tyr Gly
225                 230                 235                 240

Leu Ser Asn Gln Xaa Ala Xaa Ala Ile Ser Asp His Tyr Pro Val Glu
                245                 250                 255

Val Thr Leu Xaa Xaa Xaa
            260
```

<210> SEQ ID NO 23
<211> LENGTH: 29
<212> TYPE: DNA
<213> ORGANISM: Artificial Sequence
<220> FEATURE:
<223> OTHER INFORMATION: synthetic PCR mutagenesis forward primer to introduce S-205 insertion

<400> SEQUENCE: 23
gacaccacag tatcaaaatc gactcattg                                29

<210> SEQ ID NO 24
<211> LENGTH: 29
<212> TYPE: DNA
<213> ORGANISM: Artificial Sequence
<220> FEATURE:
<223> OTHER INFORMATION: synthetic PCR mutagenesis forward primer to introduce S-205 insertion

<400> SEQUENCE: 24
caatgagtcg attttgatac tgtggtgtc                                29

<210> SEQ ID NO 25

```
<211> LENGTH: 28
<212> TYPE: DNA
<213> ORGANISM: Artificial Sequence
<220> FEATURE:
<223> OTHER INFORMATION: synthetic PCR forward primer to introduce Nde I
      and Xho I restriction sites into untagged version
      of K- and KS-DNase mutants

<400> SEQUENCE: 25
aggagatata catatgggta cccttcgc                                          28

<210> SEQ ID NO 26
<211> LENGTH: 25
<212> TYPE: DNA
<213> ORGANISM: Artificial Sequence
<220> FEATURE:
<223> OTHER INFORMATION: synthetic PCR reverse primer to introduce Nde I
      and Xho I restriction sites into untagged version
      of K- and KS-DNase mutants

<400> SEQUENCE: 26
gttaattaag cctcgagtta accgg                                             25

<210> SEQ ID NO 27
<211> LENGTH: 36
<212> TYPE: DNA
<213> ORGANISM: Artificial Sequence
<220> FEATURE:
<223> OTHER INFORMATION: synthetic PCR forward primer to introduce Nde I
      and Xho I restriction sites into His-tagged
      version of K- and KS-DNase mutants

<400> SEQUENCE: 27
aggagatata catatgggta cccttcgcat tgccgc                                 36

<210> SEQ ID NO 28
<211> LENGTH: 57
<212> TYPE: DNA
<213> ORGANISM: Artificial Sequence
<220> FEATURE:
<223> OTHER INFORMATION: synthetic PCR reverse primer to introduce Nde I
      and Xho I restriction sites into His-tagged
      version of K- and KS-DNase mutants

<400> SEQUENCE: 28
gtggtggtgc tcgaggggtc cctgaaagag gacttcaaga ccggtcatta aggttac          57

<210> SEQ ID NO 29
<211> LENGTH: 8
<212> TYPE: PRT
<213> ORGANISM: Artificial Sequence
<220> FEATURE:
<223> OTHER INFORMATION: synthetic HRV-3C protease clavage site

<400> SEQUENCE: 29

Leu Glu Val Leu Phe Gln Gly Pro
 1               5
```

MODIFIED DNASE COMPOSITIONS AND METHODS OF USE THEREOF

CROSS-REFERENCE TO RELATED PATENT APPLICATIONS

The present application claims benefit of priority to U.S. Provisional Patent Application No. 61/168,490, filed Apr. 10, 2009, which is incorporated by reference for all purposes.

BACKGROUND OF THE INVENTION

A variety of uses are known for DNases. For example, DNases are useful for removing or degrading DNA from samples containing RNA and/or protein. This is useful, for example, when DNA in a sample interferes with manipulation or detection of the RNA or protein. As an example, DNase is useful for removing DNA from a sample prior to performing a reverse transcription reaction.

BRIEF SUMMARY OF THE INVENTION

This invention provides for synthetic or isolated nucleic acid comprising a polynucleotide encoding a polypeptide comprising a DNase I. In some embodiments, the DNase has an amino acid sequence comprising:
a. SEQ ID NO:1 and SEQ ID NO:2; and
b. SEQ ID NO: 3 or SEQ ID NO:4, or both SEQ ID NO: 3 and SEQ ID NO:4.

In some embodiments, the DNase has an amino acid sequence at least 70% (e.g., at least 99, 98, 95, 90, 85, 80, 75, 70) identical to SEQ ID NO:18. In some embodiments, the DNase has an amino acid sequence at least 70% (e.g., at least 99, 98, 95, 90, 85, 80, 75, 70) identical to SEQ ID NO:6. In some embodiments, the polypeptide further comprises a heterologous sequence-non-specific double-stranded DNA binding domain. In some embodiments, the DNA binding domain is selected from the group consisting of a DNA binding domain from a Maf proto-oncogene transcription factor, an Sso family DNA binding protein, and a HMf transcription factor.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNase I further comprises
d. ADTTX$_7$SX$_8$X$_9$TX$_{10}$CAYDRIVVAG (SEQ ID NO:4), wherein X$_7$ is A, S, or V; X$_8$ is T, S, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

The present invention also provides an expression cassette comprising a promoter operably linked to nucleic acid comprising a polynucleotide encoding a polypeptide comprising a heat-labile DNase I, the DNase having an amino acid sequence comprising:
a. SEQ ID NO:1 and SEQ ID NO:2; and
b. SEQ ID NO: 3, SEQ ID NO:4 or both SEQ ID NO: 3 and SEQ ID NO:4.

In some embodiments, the DNase has an amino acid sequence at least 70% (e.g., at least 99, 98, 95, 90, 85, 80, 75, 70) identical to SEQ ID NO:18. In some embodiments, the DNase has an amino acid sequence at least 70% (e.g., at least 99, 98, 95, 90, 85, 80, 75, 70) identical to SEQ ID NO:6. In some embodiments, the polypeptide further comprises a heterologous sequence non-specific DNA binding domain. In some embodiments, the DNA binding domain is selected from the group consisting of a DNA binding domain from a Maf proto-oncogene transcription factor, an Sso family DNA binding protein and a HMf transcription factor.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNase I further comprises
d. ADTTX$_7$SX$_8$X$_9$TX$_{10}$CAYDRIVVAG (SEQ ID NO:4), wherein X$_7$ is A, S, or V, X$_8$ is T, S, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

The present invention also provides for a cell transformed with an expression cassette comprising a promoter operably linked to nucleic acid comprising a polynucleotide encoding a polypeptide comprising a DNase I, the DNase having an amino acid sequence comprising:
a. SEQ ID NO:1 and SEQ ID NO:2; and
b. SEQ ID NO: 3, SEQ ID NO:4 or both SEQ ID NO: 3 and SEQ ID NO:4.

In some embodiments, the cell is a yeast cell. In some embodiments, the cell is a bacterial cell.

In some embodiments, the DNase has an amino acid sequence at least 70% (e.g., at least 99, 98, 95, 90, 85, 80, 75, 70) identical to SEQ ID NO:18. In some embodiments, the DNase has an amino acid sequence at least 70% (e.g., at least 99, 98, 95, 90, 85, 80, 75, 70) identical to SEQ ID NO:6. In some embodiments, the polypeptide further comprises a heterologous sequence-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

The present invention also provides methods of making a polypeptide having DNase activity. In some embodiments, the method comprises culturing a host cell under conditions to produce the polypeptide, thereby making the polypeptide. In some embodiments, the host cell is transformed with an expression cassette comprising a promoter operably linked to nucleic acid comprising a polynucleotide encoding a polypeptide comprising a DNase I, the DNase having an amino acid sequence comprising:
a. SEQ ID NO:1 and SEQ ID NO:2; and
b. SEQ ID NO: 3, SEQ ID NO:4 or both SEQ ID NO: 3 and SEQ ID NO:4.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNase I further comprises
d. ADTTX$_7$SX$_8$X$_9$TX$_{10}$CAYDRIVVAG (SEQ ID NO:4), wherein X$_7$ is A, S, or V, X$_8$ is T, S, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

In some embodiments, the polypeptide is secreted by the host cell. Exemplary host cells include, but are not limited to bacteria (e.g., *E. coli*) and yeast.

The present invention also provides isolated polypeptides made by the above method (or as described elsewhere herein). In some embodiments, the DNase has an amino acid sequence at least 70% (e.g., at least 99, 98, 95, 90, 85, 80, 75, 70) identical to SEQ ID NO:18. In some embodiments, the DNase has an amino acid sequence at least 70% {e.g., at least 99, 98, 95, 90, 85, 80, 75, 70} identical to SEQ ID NO:6. In some embodiments, the polypeptide further comprises a heterologous sequence-non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNase I further comprises
d. ADTTX$_7$SX$_8$X$_9$TX$_{10}$CAYDRIVVAG (SEQ ID NO:4), wherein X$_7$ is A, S, or V, X$_8$ is T, S, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

The present invention also provides a reaction mixture comprising a DNase that is heat-labile, hyperactive, or both, fused to a heterologous sequence non-specific DNA binding domain.

In some embodiments, the DNase comprises:
a. SEQ ID NO:1 and SEQ ID NO:2; and/or
b. SEQ ID NO: 3 or SEQ ID NO:4, or both SEQ ID NO: 3 and SEQ ID NO:4.

In some embodiments, the reaction mixture further comprises a nucleic acid sample, wherein the sample comprises RNA, DNA and/or protein. In some embodiments, the reaction mixture further comprises a topoisomerase.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNase I further comprises
d. ADTTX$_7$SX$_8$X$_9$TX$_{10}$CAYDRIVVAG (SEQ ID NO:4), wherein X$_7$ is A, S, or V, X$_8$ is T, S, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

The present invention also provides reaction mixtures comprising a DNase that is heat-labile, hyperactive, or both; and a topoisomerase.

In some embodiments, the DNase comprises:
a. SEQ ID NO:1 and SEQ ID NO:2; and/or
b. SEQ ID NO: 3 or SEQ ID NO:4, or both SEQ ID NO: 3 and SEQ ID NO:4.

In some embodiments, the DNase has an amino acid sequence at least 70% (e.g., at least 99, 98, 95, 90, 85, 80, 75, 70) identical to SEQ ID NO:18. In some embodiments, the DNase has an amino acid sequence at least 70% (e.g., at least 99, 98, 95, 90, 85, 80, 75, 70) identical to SEQ ID NO:6. In some embodiments, the topoisomerase is a Type IB topoisomerase. In some embodiments, the topoisomerase is DraTopIB.

In some embodiments, the reaction mixture further comprises a nucleic acid sample, wherein the sample comprises RNA, DNA, and/or protein. In some embodiments, the reaction mixture further comprises a reverse transcriptase.

In some embodiments, the reaction mixture further comprises the DNase has an amino acid sequence at least 70% {e.g., at least 99, 98, 95, 90, 85, 80, 75, 70} identical to SEQ ID NO:18.

The present invention also provides for kits comprising a DNase that is heat-labile, hyperactive, or both, fused to a heterologous sequence non-specific DNA binding domain. In some embodiments, the DNase comprises:
a. SEQ ID NO:1 and SEQ ID NO:2; and/or
b. SEQ ID NO: 3 or SEQ ID NO:4, or both SEQ ID NO: 3 and SEQ ID NO:4.

In some embodiments, the kit further comprises a reverse transcriptase. In some embodiments, the kit further comprises a topoisomerase.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNaseI further comprises
d. ADTTX$_7$SX$_8$X$_9$TX$_{10}$CAYDRIVVAG (SEQ ID NO:4), wherein X$_7$ is A, S, or V, X$_8$ is T, 5, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

The present invention also provides a kit comprising a DNase that is heat-labile, hyperactive, or both; and a topoisomerase. In some embodiments, the topoisomerase is a Type LB topoisomerase. In some embodiments, the topoisomerase is DraTopIB In some embodiments, the DNase comprises:

a. SEQ ID NO:1 and SEQ ID NO:2; and/or
b. SEQ ID NO: 3 or SEQ ID NO:4, or both SEQ ID NO: 3 and SEQ ID NO:4.

In some embodiments, the kit further comprises a reverse transcriptase.

The present invention also provides for methods for removing DNA from a sample. In some embodiments, the method comprises incubating the sample with a DNase, wherein the incubating step is performed under conditions sufficient to degrade at least a majority of the DNA in the sample. In some embodiments, the DNase is inactivated following the incubating step. In some embodiments, the sample is heated, thereby substantially eliminating the DNase activity of the polypeptide. In some embodiments, the inactivation step comprises chelating or removal of ions (e.g., divalent cations) or other molecules in the solution necessary for DNase activity. In some embodiments, a combination of the aforementioned inactivation methods is used.

In some embodiments, the DNase comprises:
a. SEQ ID NO:1 and SEQ ID NO:2; and/or
b. SEQ ID NO: 3 or SEQ ID NO:4, or both SEQ ID NO: 3 and SEQ ID NO:4.

In some embodiments, the DNase has an amino acid sequence at least 70% (e.g., at least 99, 98, 95, 90, 85, 80, 75, 70) identical to SEQ ID NO:18. In some embodiments, the DNase has an amino acid sequence at least 70% (e.g., at least 99, 98, 95, 90, 85, 80, 75, 70) identical to SEQ ID NO:6.

In some embodiments, the polypeptide further comprises a heterologous sequence non-specific soluble-stranded DNA binding domain. In some embodiments, the DNA binding domain is selected from the group consisting of a DNA binding domain from a Maf proto-oncogene transcription factor, an Sso family DNA binding protein and a HMf transcription factor.

In some embodiments, the incubating step comprises incubating the sample with a topoisomerase.

In some embodiments, the method further comprises following the heating step performing a reverse transcription reaction on RNA present in the sample. In some embodiments, the reverse transcription reaction is performed by adding a reverse transcriptase before, during or following the heating step.

In some embodiments, the polypeptide comprises a DNase I, the DNase having an amino acid sequence comprising:
a. AAFNIX$_1$X$_2$FGX$_3$TKMSN (SEQ ID NO:1), wherein X$_1$ and X$_3$ are basic amino acids and X$_2$ is S or T;
b. SEPLGRX$_4$X$_5$YKE (SEQ ID NO:2), wherein X$_4$ is a basic amino acid and X$_5$ is S, T, or N; and
c. FALVX$_6$LH (SEQ ID NO:3), wherein X$_6$ is A or P.

In some embodiments, X$_1$ and X$_3$ are R (SEQ ID NO:20) and X$_4$ is K (SEQ ID NO:21). In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:19. In some embodiments, the DNase has an amino acid sequence at least 70% identical to SEQ ID NO:6.

In some embodiments, the DNase I further comprises
d. ADTTX$_7$SX$_8$X$_9$TX$_{10}$CAYDRIVVAG (SEQ ID NO:4), wherein X$_7$ is A, S, or V, X$_8$ is T, S, or K; X$_9$ is S or P; and X$_{10}$ is N or H.

In some embodiments, the DNase has an amino acid sequence at least 70% (e.g., at least 99, 98, 95, 90, 85, 80, 75, 70) identical to SEQ ID NO:18. In some embodiments, the DNase comprises SEQ ID NO:18.

In some embodiments, the polypeptide further comprises a heterologous sequence—non-specific double-stranded DNA binding domain. In some embodiments, the DNA binding domain is selected from the group consisting of a DNA binding domain from a Maf proto-oncogene transcription factor, an Sso family DNA binding protein and a HMf transcription factor.

Other embodiments of the invention will be clear from reading the remainder of this document.

DEFINITIONS

"DNase I" is a naturally-occurring or synthetic (e.g., mutant) phosphodiesterase capable of hydrolyzing polydeoxyribonucleic acid. Bovine DNase I has been extensively studied biochemically. See, e.g., Moore, in *The Enzymes* (Boyer, P. D., ed), pp. 281-296, Academic press, New York (1981). The complete amino acid sequence for bovine DNase I is known (Liao, et al., *J. Biol. Chem.* 248:1489-1495 (1973); Oefner, et al., *J. Mol. Biol.* 192:605-632 (1986); Lahm, et al., *J. Mol. Biol.* 221:645-667 (1991)), and DNA encoding bovine DNase I has been cloned and expressed (Worrall, et al., *J. Biol. Chem.* 265:21889-21895 (1990)). The structure of bovine DNase I has been determined by X-ray crystallography. Suck, et al., *EMBO J.* 3:2423-2430 (1984); Suck, et al., *Nature* 321:620-625 (1986); Oefner, et al., *J. Mol. Biol.* 192: 605-632 (1986). DNase I enzymes from different species are highly related as shown in FIG. 1.

A 'heat-labile DNase" refers to a DNase whose DNase activity is substantially eliminated following incubation at 50° C. or greater for 5 minutes or longer. "Substantially eliminated" means that the DNase has less than 10%, e.g., less than 5%, 1% or less, compared to the enzyme's activity prior to the incubation.

"Thermostable" refers to the ability of an enzyme to retain enzymatic activity following or during incubation at a temperature between 50-95° C. (e.g., for at least 10 minutes).

A "synthetic" nucleic acid refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette can comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

"Heterologous sequences" are those that are not operatively linked or are not contiguous to each other in nature. Regulatory element sequences, such as promoters, UTRs or 3' end termination sequences that do not originate in nature from the same gene as the coding sequence originates from, are considered heterologous to said coding sequence. Elements operatively linked in nature and contiguous to each other are not heterologous to each other. For instance, the nucleic acid is can be recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "host cell" refers to a cell from any organism. Exemplary host cells are derived from plants, bacteria, yeast, fungi, insects or animals. Methods for introducing polynucleotide sequences into various types of host cells are well known in the art.

An "expression cassette" refers to a nucleic acid construct, which when introduced into a host cell, results in transcription and/or translation of a RNA or polypeptide, respectively.

The term "isolated," when applied to a nucleic acid or protein, denotes that the nucleic acid or protein is essentially free of other cellular components with which it is associated in the natural state. It is optionally in a homogeneous state and can be in either a dry or aqueous solution. Purity and homogeneity are typically determined using analytical chemistry techniques such as polyacrylamide gel electrophoresis or high performance liquid chromatography.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are optionally metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (e.g., a DNase), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, designated region as measured using one of the following sequence comparison algorithms or by manual alignment and visual inspection, or across the entire sequence where not indicated. The invention provides polypeptides that are substantially identical to the DNases exemplified herein (e.g., SEQ ID NO: 1, 2, 3, 4, 5, 6, 7, 8 9, 10, 11, 12, 13, 14, 15, 16, 17, 18, or 19).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. Unless indicated otherwise, default parameters can be assumed. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

BRIEF DESCRIPTION OF THE DRAWINGS

FIG. 1 illustrates an alignment of different DNase I amino acid sequences (SEQ ID NOS:6, 5, 8, 7, 10, 9, 11, 12 and 13, respectively) and provides a consensus sequence (SEQ ID NO:22) at the bottom of the alignment. Capitalized amino acids are conserved between DNases in the alignment, whereas lower case amino acids indicate a position where there is not a complete consensus and the amino acid at that position reflects the most commonly occurring amino acid. However, those of skill in the art will appreciate that other amino acids that occur at the position (as well as conservative substitutions) can also be used.

DETAILED DESCRIPTION

I. Introduction

Figure 2:
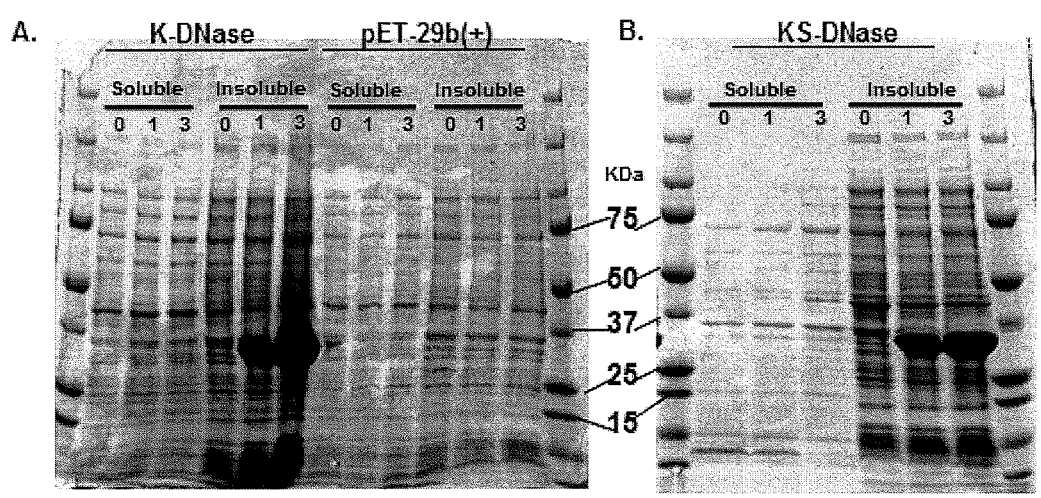
FIG. 2: This figure shows the expression of His-tagged K- and KS-DNase mutant proteins in *E. coli* BL21(DE3) cells. The numbers written on top of the lanes indicate the following times; "0" indicates sample collected just prior to induction, and 1 and 3 indicate samples collected at 1 hour and 3 hours post-induction with IPTG. His-tagged K- and KS-DNase mutant proteins have a calculated molecular weight of about 32 KDa.

The present invention provides for a variety of compositions and methods that involve the use of modified DNases to degrade DNA. For example, DNases are provided that are heat-labile, thereby allowing for heating of a reaction to substantially eliminate DNase activity without the need for separation of the DNase from the rest of a sample of interest. Also provided are hyperactivity mutations, optionally in combination with the heat-lability mutations. Any of the above-described DNases can be further fused to a DNA binding domain, thereby improving activity of the DNase. Optionally, the DNases of the invention can be used in combination with a topoisomerase to further improve activity.

II. DNases

A. General

Any DNase can be used in many aspects of the invention. A wide variety of DNases are known and can be categorized as e.g., DNase I, DNase II, DNase III, DNase IV, DNase V, DNase VI, DNase VII, DNase VIII, etc. Any and all of these DNases can be improved by fusion with a DNA binding domain and/or used in combination with a topoisomerase as described below.

B. Hyperactivity Mutations

Figure 1:
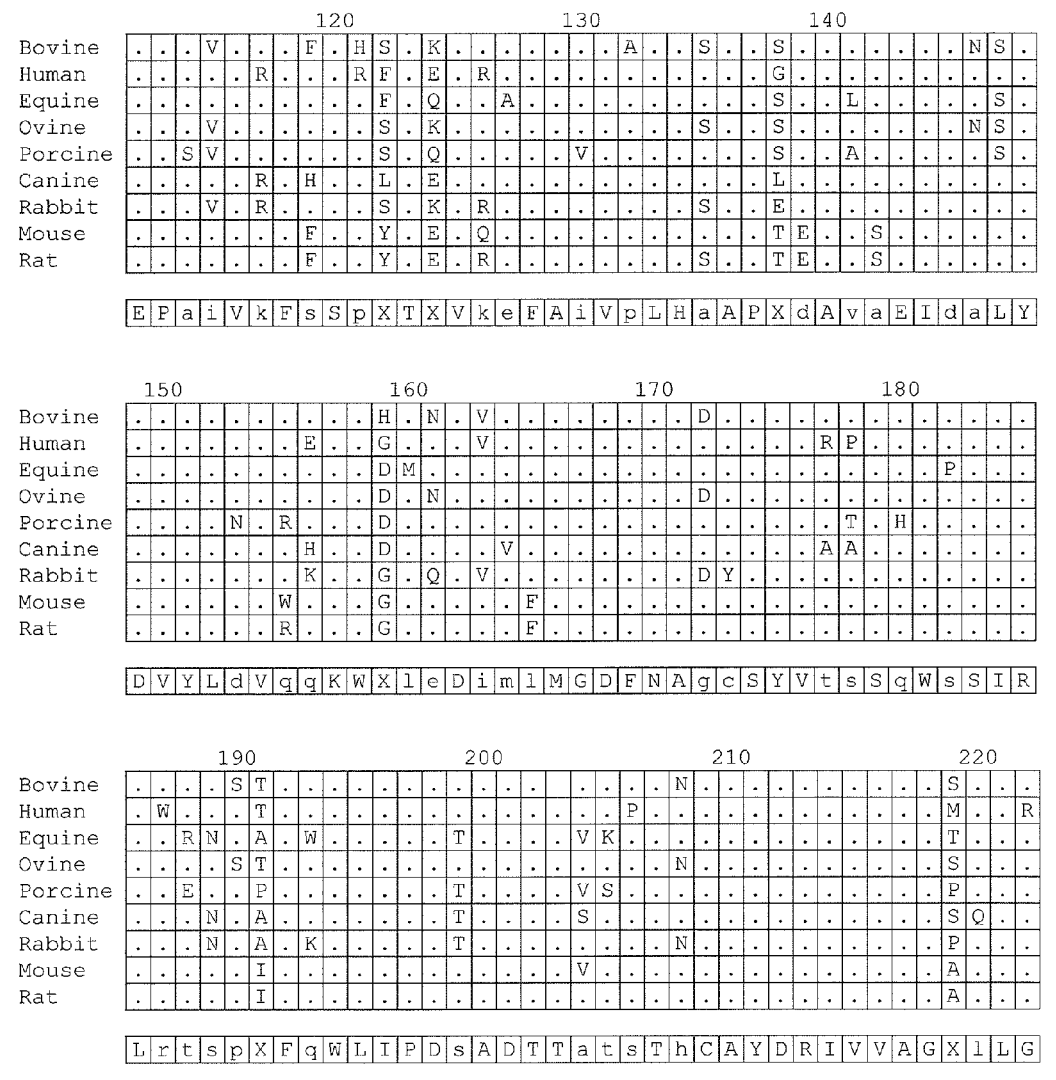

Hyperactivity mutations refer to mutations in one or more of various positions in a DNase I polypeptide that result in a reduced Km of the DNase for DNA and an increased catalytic efficiency. A hyperactive mutant DNase I could also exhibit increased tolerance to salt due to enhanced binding affinity for the dsDNA substrate. In some embodiments, a hyperactivity mutation of the invention improves at least one of these criteria by at least, e.g., 5%, 10%, 25%, 50% compared to an unmodified native control DNase I. Methods for making such determinations are known in the art. See, e.g., Clark et al., *J. Biol. Chem.* 273(19):11701-11708 (1998). Exemplary mutations include, but are not limited to, insertion of positively charged amino acids at one or more of the following positions relative to human DNase I: □9, E13, T14, H49, N74, and T205. Without intending to limit the scope of the invention, it is believed that the above-positions are at the DNA-binding interface of the DNase and therefore replacing the native amino acids with positively charged amino acids increase binding to negative charged DNA. In some embodiments, the mutations are one or more of Q9R, E13R, T14K, H49K, N74K, and T205K, though as noted above other positively charged (e.g., basic) amino acids can also be used. Positively charged amino acids include: histidine (H), arginine (R), lysine (K), asparagine (N) and glutamine (Q). In some embodiments, the hyperactive DNase I comprises two of, or all three of, the Q9R, E13R, and N74K mutations. Although in the above discussion (indeed, in general throughout the specification) positions are provided relative to the human DNase I sequence, it will be appreciated that the mutations can be introduced into the corresponding positions of other DNaseI polypeptides, including but not limited to those specifically provided herein, (e.g., in the Sequence listing). Corresponding positions in other DNaseI polypeptides can be determined using computer-based alignment programs as described herein with reference to percent identities for nucleotide or amino acid sequences. Such corresponding positions can also be determined from the alignment provided in FIG. 1.

In view of the significant number of native DNase I sequences known in the art, the inventors have been able to derive consensus sequences for DNase I sequences having the hyperactivity mutations. For example, DNase I polypeptides having the motif defined by SEQ ID NO:1 include positively-charged amino acids at the Q9 and E13 positions. DNase I polypeptides having the motif defined by SEQ ID NO:2 include positively-charged amino acids at the N74 position. In some embodiments, the hyperactive DNase I polypeptides of the invention comprise SEQ ID NO:1 and 2 (as well as intervening and flanking amino acid sequences consistent with the known DNase I sequences, as well as the sequences and information provided herein such that the polypeptide has DNase activity).

In some embodiments, one or more hyperactivity mutation is included in a DNase that is substantially identical to SEQ ID NO: 1, 2, 3, 4, 5, 6, 7, 8, 9, 10, 11, 12, 13, 14, 15, 16, 17, 18, or 19. As a non-limiting example, in some embodiments, the invention provides for a DNase that is substantially identical (e.g., 80% or 90% or 95% or 100%) to the human, ovine, bovine or equine DNase I sequences provided herein, except that one, two or all three of the positions in the DNases corresponding to Q9, E13, and N74 are a positively charged amino acid (e.g., H, R, or K) and optionally one or more heat lability mutations as described below.

Hyperactivity mutations can be included with other sorts of mutations (including but not limited to heat lability mutations) in one DNase polypeptide.

C. Heat Lability Mutations

Heat lability mutations refer to one or more mutations in various positions in a DNase I polypeptide that result in heat lability for a particular DNase. Several amino acid positions in DNases have been described as causing heat lability in some organisms that live in cooler climates. For example, Leu130 and Ser-205 (i.e., inserted between the Ala and Thr in human DNase I) induce heat lability in a DNase. See, e.g., Takeshita, et al. *Biochem. J.* 357:473-480 (2001); Takeshita, et al., *Eur. J. Biochem.* 270:307-314 (2003). Although above discussion (indeed, in general throughout the specification) positions are provided relative to the human DNase I sequence, it will be appreciated that the mutations can be introduced into the corresponding positions of other DNaseI polypeptides, including but not limited to those specifically provided herein, (e.g., in the Sequence listing). Thus, in some embodiments, a DNase of the invention having heat lability will have one or more of the following consensus motifs:
SEQ ID NO:3
Motif with Leu130
FALVX$_6$LH, wherein X$_6$ is A or P
SEQ ID NO:4
Motif with Ser-205

ADTTX$_7$SX$_8$X$_9$TX$_{10}$CAYDRIVVAG, wherein X$_7$ is A, S, or V, X$_8$ is T, S, or K; X$_9$ is S or P; and X$_{10}$ is N or H In some embodiments, a DNase of the invention comprises both SEQ ID NO: 3 and 4.

In some embodiments, one or more heat lability mutation is included in a DNase that is substantially identical to SEQ ID NO: 1, 2, 3, 4, 5, 6, 7, 8, 9, 10, 11, 12, 13, 14, 15, 16, 17, 18, or 19. As a non-limiting example, in some embodiments, the invention provides for a DNase that is substantially identical (e.g., 80% or 90% or 95% or 100%) to the human, ovine, bovine or equine DNase I sequences provided herein, except that the sequences have one or both of amino acids corresponding to Leu130 or Ser-205, and optionally one or more hyperactivity mutations as described above.

Heat lability mutations can be included with other sorts of mutations (including but not limited to hyperactivity mutations) in one DNase polypeptide. Thus in some embodiments, the invention provides a DNase that is both heat labile and hyperactive. In some embodiments, such a DNase comprises at least one or both of SEQ ID NO:1 and SEQ ID NO:2 (conferring hyperactivity) and one or both of SEQ ID NO:3 and SEQ ID NO:4 (conferring heat lability).

D. Nucleic Acids Encoding DNases

The present invention also provides for nucleic acids that encode the DNases of the invention. In some embodiments, the nucleic acids of the invention are synthetic, isolated, or both.

Nucleic acids encoding the DNase polypeptides of the invention can be used for recombinant expression of the polypeptides. In these methods, the nucleic acids encoding the proteins of interest are introduced into suitable host cells, e.g., bacteria, yeast, insect cells, plant cells or animal cells (e.g., CHO cells, COS cells, etc.), followed by induction of the cells to produce large amounts of the protein. The invention relies on routine techniques in the field of recombinant genetics, well known to those of ordinary skill in the art. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In some embodiments, amplification techniques such as polymerase chain reaction technology (PCR) can be used to amplify and/or mutate desired nucleic acid sequences. Polymerase chain reaction (PCR) or other in vitro amplification methods may also be useful, for example, to clone nucleic acid sequences that code for proteins to be expressed or for other purposes (for a general overview of PCR, see *PCR Protocols: A Guide to Methods and Applications* (Innis et al., eds., 1990).

The particular procedure used to introduce the genetic material into the host cell for expression of the polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra).

A variety of vectors can be used to transport the genetic information into the cell. Any of the conventional vectors used for expression of recombinant proteins in prokaryotic and eukaryotic cells may be used. Expression vectors for mammalian cells can contain, for example, regulatory elements from eukaryotic viruses.

The expression vector typically contains a transcription unit or expression cassette that contains all the elements required for the expression of the polypeptide DNA in the host cells. In some embodiments, the expression cassette contains a promoter operably linked to the DNA sequence encoding a polypeptide and signals required for efficient polyadenylation of the transcript.

III. DNA Binding Domain Fusions

Optionally, the DNases of the invention can be linked (including but not limited to fused as a fusion protein) to a polypeptide comprises a DNA binding domain. In some embodiments, the DNA binding domain is a sequence non-specific DNA binding domain. Thus in some embodiments, the DNA binding domain is fused to a DNase having heat lability, hyperactivity, or both as set forth herein. In cases where the DNA binding domain is fused to a heat labile DNase, in some embodiments the DNA binding domain itself does not significantly improve the heat stability of the resulting linked DNase.

A double-stranded sequence-non-specific nucleic acid binding domain is a polypeptide sequence that binds to double-stranded nucleic acid in a sequence-independent manner, i.e., binding does not exhibit a gross preference for a particular sequence. In some embodiments, double-stranded nucleic acid binding proteins exhibit a 10-fold or higher affinity for double-stranded versus single-stranded nucleic acids. The double-stranded nucleic acid binding proteins in some embodiments of the invention are thermostable. Examples of double-stranded DNA binding proteins include, but are not limited to, at least the DNA binding domain of a Maf or a member of the Maf proto-oncogene family of transcription factors (e.g., MafF, MafG and MafK (see, e.g., *J. Mol. Biol.* 376, 913-925 (2008) or a DNA binding portion thereof), or the Archaeal small basic DNA binding proteins Sac7d and Sso7d (see, e.g., Choli et al., *Biochimica et Biophysica Acta* 950:193-203 (1988); Baumann et al., *Structural Biol.* 1:808-819 (1994); and Gao et al, *Nature Struc. Biol.* 5:782-786, 1998), and Archael HMf-like proteins (see, e.g., Stanch et al., *J. Molec. Biol.* 255:187-203 (1996); Sandman et al., *Gene* 150:207-208 (1994).

Sso7d and Sac7d are small (in some embodiments, about 7 kD), basic chromosomal proteins from the hyperthermophilic archaeabacteria *Sulfolobus solfataricus* and *S. acidocaldarius*, respectively. See, e.g., WO/2004/037979. These proteins are lysine-rich and have high thermal, acid and chemical stability. They bind DNA in a sequence-independent manner and when bound, increase the T$_M$ of DNA by up to 40° C. under some conditions (McAfee et al., *Biochemistry* 34:10063-10077 (1995)). Optionally, one can use L54Δ, a truncated form of Sso7d. See, e.g., Erlet Shehi, et al. *Biochemistry* 42, 8362-8368 (2003). L54Δ maintains the same sequence-independent DNA binding property as the wild type Sso7d protein, but has a reduced thermal stability compared to the wild type protein. See, e.g., Erlet Shehi, et al. *Biochemistry* 42, 8362-8368 (2003). In some embodiments, the DNA binding domains of the invention are at least 70%, 80%, 95%, or 95% identical to Sso7d, Sac7d or L54Δ of *Sulfolobus solfataricus* or *S. acidocaldarius*.

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). In some embodiments, a dimeric HMf-like protein can be covalently linked (e.g., fused) to the N- or C-terminus of a DNase of the invention, e.g., a DNase with heat lability, hyperactivity, or both.

The activity of the sequence non-specific double-stranded nucleic acid binding domains can be assessed using a variety of assays. Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with labeled DNA, either double-stranded or single-stranded, in the appropriate buffer. The mixture is filtered through a membrane (e.g., nitrocellulose), which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. Alternatively, binding activity can be assessed by a gel shift assay in which labeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

Novel sequence non-specific double-stranded nucleic acid binding proteins of the invention can also be isolated by taking advantage of their DNA binding activity, for instance by purification on DNA-immobilized (e.g., on cellulose) columns. The isolated proteins can then be further purified by conventional means, sequenced, and the genes cloned by conventional means via PCR. Proteins overexpressed from these clones can then be tested by any of the means described above.

The DNase and the nucleic acid-binding domain can be joined by methods well known to those of skill in the art. These methods include, for example, chemical and recombinant methods for joining or producing fusion proteins. Such a fusion product can be made by, for example, ligating the appropriate nucleic acid sequences encoding the desired amino acid sequences to each other by methods known in the art, in the proper coding frame, and expressing the product by methods known in the art. Chemical methods of joining the heterologous domains are described, e.g., in *Bioconjugate Techniques*, Hermanson, Ed., Academic Press (1996). These include, for example, derivitization for the purpose of linking the moieties to each other, either directly or through a linking compound, by methods that are known in the art of protein chemistry.

For example, in one chemical conjugation embodiment, a heterobifunctional coupling reagent can be used to link the DNase and the nucleic acid binding domain. In some embodiments, the reagent will result in formation of an intermolecular disulfide bond between the two moieties. Other types of coupling reagents that are useful in this capacity for the present invention include, but are not limited to, those described in U.S. Pat. No. 4,545,985. In some embodiments, an intermolecular disulfide can conveniently be formed between cysteines in each moiety, which occur naturally or are inserted by genetic engineering. Exemplary linking moieties can also include, e.g., thioether linkages between heterobifunctional crosslinking reagents or specific low pH cleavable crosslinkers or specific protease cleavable linkers or other cleavable or noncleavable chemical linkages.

Fusion proteins can comprise a peptidyl bond formed between moieties that are separately synthesized by standard peptide synthesis chemistry or recombinantly. In addition, non-naturally-occurring amino acids or chemical amino acid analogs can be introduced as a substitution or addition into the sequence. Non-naturally-occurring amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, and Nα-methyl amino acids.

In a specific embodiment, the coding sequences of each polypeptide in the fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Other methods of joining the domains include ionic binding by expressing negative and positive tails and indirect binding through antibodies and streptavidin-biotin interactions. (See, e.g., *Bioconjugate Techniques*, supra). The domains may also be joined together through an intermediate interacting sequence.

IV. Topoisomerases

Optionally, one or more topoisomerases can be used in combination with the DNases of the invention (including but not limited to those linked to DNA binding domains). Without intending to limit the scope of the invention, it is believed that inclusion of a topoisomerase with a DNase of the invention in the presence of DNA will result in more efficient degradation of the DNA, especially if the DNA is eukaryotic or other DNA that has higher three-dimensional structures (e.g., supercoiled) and/or is in contact with chromosomal proteins including but not limited to histones. Optionally, the topoisomerase is heat labile (e.g., will be inactivated under the same heat conditions as the heat labile DNase used with the topoisomerase). It will be appreciated that it is desirable to select a topoisomerase whose conditions for optimal enzyme activity should be compatible with the conditions for which the DNase is active.

In some embodiments, the topoisomerase is selected from a Type I or Type II topoisomerase. See, e.g., Champoux J J, "DNA topoisomerases: structure, function, and mechanism" *Annu. Rev. Biochem.* 70: 369-413 (2001). In some embodiments, the topoisomerase is selected from a Type IA, IB, or IC topoisomerase. In some embodiments, the topoisomerase is selected from type IIA and type IIB topoisomerase. Examples of type IIA topoisomerases include, but are not limited to, eukaryotic topo II, *E. coli* gyrase, and *E. coli* topo IV. Examples of type IIB topoisomerase include topo VI.

In some embodiments, the topoisomerase is DraTopIB, a topoisomerase IB from bacteria *Deinococcus radiodurans*. See, e.g., Berit Olsen Krogh and Stewart Shuman, *Proc. Natl. Acad. Sci. USA*, 99(4):1853-1858 (2002).

A toposisomerase can be combined as a separate molecule with a DNases of the invention (e.g., in a kit or reaction mixture). In such combinations, the topoisomerase can remove supercoiling from supercoiled DNA, thereby making the DNA more available as a substrate for the DNase. Optionally, in some embodiments, the topoisomerase can be linked (e.g., as a fusion protein) to a DNase of the invention. Such linkages can be evaluated to confirm that the particular combination of topoisomerase and DNase result in optimal activity (e.g., in comparison to the DNase alone or to the mixture of non-linked topoisomerase and DNase).

A topoisomerase can be used in combination with any DNase described herein. For example, in some embodiments, the topoisomerase is used in combination (separately or as a fusion) with a DNase/DNA binding protein fusion.

V. Methods

The DNases of the invention can be used in a wide range of molecular techniques where it is desirable to degrade DNA in a sample. This can be desirable, for example, when one wants to detect or purify RNA in a sample (for example in a reverse transcription reaction) or where one wishes to detect protein or other non-DNA molecules in a sample where DNA could interfere with appropriate detection. DNases can also be used in various DNA protection assays (e.g., to determine the presence, absence and/or location of binding of a protein or other molecule to DNA). In some embodiments, a DNase of the invention can be used, for example, to decrease or prevent clumping of cells, including but not limited to cultured cells. The DNases can also be used to generate partial digestions of DNA where DNA fragments are desired, e.g., for genomic or other nucleic acid library preparation.

In some embodiments, the DNase is used in a method of purifying RNA from a sample by digesting DNA present in the sample. In some embodiments, a DNase of the invention is used in a column-based RNA purification (i.e. through binding of RNA or nucleic acid to resins pre-loaded on the column). For example, a DNase-containing solution can be added to the column after the RNA is bound so that any DNA that are bound to the column or resin can be digested and washed away from the column before the bound RNA is eluted off the column/resin. This will ensure that the purified RNA sample is free of any DNA contamination.

In embodiments in which a heat labile DNase is used, it can be desirable at some point in a method to inactivate the DNase. In some embodiments, the DNase is inactivated by submitting the reaction mixture comprising the DNase to a heating step. In some embodiments, the reaction mixture is raised to a temperature for a period of time that substantially eliminates (e.g., reduces activity by at least 90, 95, 99% or more, e.g., 100%) the activity of the DNase. For example, in some embodiments, the reaction mixture is raised to at least 45° C. (e.g., at least 50°, e.g., 50°-90°, 50°-80°, 50°-100°, etc.). In some embodiments the elevated temperature is maintained for a sufficient time to substantially eliminate the DNase activity and then lowered, optionally to a temperature (e.g., to 35-40° C.) where further enzymatic reactions (e.g., a reverse transcriptase, DNA restriction or ligation reaction, etc.) will take place. Optionally, the heat-inactivated DNase is not removed following inactivation.

In some embodiments, the DNase is inactivated by chelation of ions (e.g., divalent ions) or other solution components necessary for DNase activity. Exemplary chelators include, e.g., EDTA. In other embodiments, the ions or other solution components necessary for DNase activity are removed from the solution comprising the DNase. In some embodiments, the solution comprising the DNase is heated and ions are removed or chelated as described above.

One additional advantage of a heat-labile DNase I is that RNA tends to undergo self-cleavage in the presence of Mg++ and at temperature greater than 60° C. If the DNase I used in removing DNA from a sample (e.g., an RNA or protein sample) needs to be heat inactivated at temperature >60° C., then the addition of EDTA is required to prevent RNA self-cleavage. The use of a heat labile DNaseI that can be inactivated at <60° C. will bypass the need of EDTA addition. Thus, in some embodiments, a DNase of the invention is used to degrade DNA in an RNA sample and is then heat inactivated at a temperature below 60° C. in the absence of EDTA or other chelating agent.

In some embodiments, the DNase (and optionally also cations or other reagents not needed or that are inhibitory in subsequent steps) is removed following degradation of DNA in a sample and prior to at least one or more subsequent enzymatic steps. A variety of methods are known for removal of DNase from reactions.

In some embodiments, where reverse transcription of RNA is to take place, a heat-labile DNase of the invention is used in combination with a reverse transcriptase (RT). In some embodiments, the reverse transcriptase is a thermostable reverse transcriptase. In some of these embodiments, the optimal temperature for activity for the thermostable RT is sufficiently high to allow in-tube inactivation of the heat labile DNase prior to the reverse transcription reaction. Optionally, the RT (thermostable or not) can be added following heat inactivation or removal of the DNase.

VI. Reaction Mixtures

The present invention provides for reaction mixtures comprising at least one DNase of the invention and a optionally a biological sample or purified portion thereof (e.g., a purified RNA, DNA, or both, and/or protein). For example, the DNase in the reaction mixture can be heat labile, hyperactive, or both and can optionally be linked to a DNA binding domain as described herein.

In some embodiments, the reaction mixtures also comprise a reverse transcriptase. In some embodiments, the reverse transcriptase is a thermostable reverse transcriptase. In some embodiments, the reaction mixture comprises reagents for use in an amplification and/or reverse transcription reaction, including but not limited to, primers (e.g., gene specific primers, random hexamer, and/or oligo dT), one or more buffer, and an enzyme stabilizer. In some embodiments, the reaction mixture further comprises the appropriate ions for enzymatic activity (e.g., $Ca^{++}$, $Mg^{++}$, $Mn^{++}$, or alternatively, lacks $Ca^{++}$, $Mg^{++}$, and/or $Mg^{++}$). In some embodiments, the reaction mixture further comprises nucleotides (including but not limited to deoxynucleotide triphosphates (dNTPs) or dideoxynucleotide triphosphates or analogs thereof). In some embodiments the nucleotides include at least 3 of the 4 DNA nucleotide triphosphates (dATP, dCTP, dGTP, dTTP) and in some embodiments all four. In some embodiments one of the four DNA nucleotides is excluded. In some embodiments, at least one nucleotide (e.g., dATP, dCTP, dGTP, or dTTP) is labeled. A variety of labels are known in the art and include, but are not limited to, fluorescent labels (e.g., FRET labels, optionally including a quencher), radiolabels, enzymes, or other tags (e.g., epitope tags, poly-His, biotin, streptavidin, etc.). In some embodiments, the reaction mixture further comprises a topoisomerase.

In some embodiments, the DNase of the invention is linked to a solid surface (including but not limited to, a bead, column, or a surface of a reaction vessel). In some embodiments, the DNase is not linked to a solid surface.

VII. Kits

The present invention also provides kits, e.g., for treating a sample to remove or degrade DNA. A kit can optionally include written instructions or electronic instructions (e.g., on a CD-ROM or DVD). Kits of the invention will typically include a case or container for holding the reagents in the kit, which can be included separately or in combination.

In some embodiments, the kits comprise at least one DNase of the invention. For example, the DNase in the reaction mixture can be heat labile, hyperactive, or both and can optionally be linked to a DNA binding domain as described herein.

In some embodiments, the kits also comprise a reverse transcriptase. In some embodiments, the reverse transcriptase is a thermostable reverse transcriptase. In some embodiments, the kit comprises reagents for use in an amplification and/or reverse transcription reaction, including but not limited to, primers (e.g., specific primers, random hexamer, and/or oligo dT), one or more buffer, and an enzyme stabilizer. In some embodiments, the kit further comprises the appropriate buffers for enzymatic activity (e.g., including or excluding $Ca^{++}$, $Mg^{++}$, and/or $Mn^{++}$ as appropriate). In some embodiments, the kit further comprises nucleotides (including but not limited to deoxynucleotides or dideoxynucleotides or analogs thereof). In some embodiments the nucleotides include at least 3 of the 4 DNA nucleotides (dATP, dCTP, dGTP, dTTP) and in some embodiments all four. In some embodiments one of the four DNA nucleotides is excluded. In some embodiments, at least one nucleotide (e.g., dATP, dCTP, dGTP, or dTTP) is labeled. A variety of labels are known in the art and include, but are not limited to, fluorescent labels (e.g., FRET labels, optionally including a quencher), radiolabels, enzymes, or other tags (e.g., epitope tags, poly-His, biotin, streptavidin, etc.). In some embodiments, the kit further comprises a topoisomerase.

Kit reagents can be configured in may different ways. For example, each enzyme can be provided in a separate container, with or without a buffer designed to optimize enzyme activity. Some exemplary kit configurations with which reagents are in which containers, is provided in the Example section.

In some embodiments, the DNase in the kit is linked to a solid surface (including but not limited to, a bead, column, or a surface of a reaction vessel). In some embodiments, the DNase is not linked to a solid surface.

EXAMPLES

The following examples are offered to illustrate, but not to limit the claimed invention.

Example 1

Possible Kit Configuration and Methods for Using a DNase of the Invention with a Reverse Transcriptase The following table provides some possible kit configurations relating the invention. One of skill in the art will appreciate that other kit configurations are also possible in view of what has been presented herein.

|  | Kit 1 | Kit 2 | Kit 3 |
|---|---|---|---|
| Tube 1 | DNase I | DNase/RTase buffer, monovalent and divalent cation, oligo dT, random hexamer, dNTPs, stabilizer | DNase I enzyme, thermal stable RTase, DNase/RTase buffer, monovalent and divalent cation, oligo dT, random |

-continued

|  | Kit 1 | Kit 2 | Kit 3 |
|---|---|---|---|
|  |  |  | hexamer, dNTPs, stabilizer |
| Tube 2 | DNase I buffer | Mixture of DNase I and thermal-stable RTase | Nuclease-free water |
| Tube 3 | RTase buffer, monovalent and divalent cation, oligo dT, random hexamer, dNTPs, stabilizer | Nuclease-free water |  |
| Tube 4 | RTase |  |  |
| Tube 5 | Nuclease-free water |  |  |

Exemplary Reaction Mix and Reaction Protocol for Using a Heat-Labile Hyperactive DNase I with Standard Reverse Transcriptase (e.g., iScript cDNA Synthesis Kit from Bio-Rad):

To remove genomic DNA (gDNA), add DNase I buffer and DNase I to the sample followed by incubation for 5 minutes or more at room temperature or 37° C. Following incubation, inactivate DNase I by heating at 55-60° C. for 5 min or more. For reverse transcription (RT), the DNase I treated sample can be used directly using the RT reagents (e.g., tubes 3 and 4 in kit 1) provided with the kit. In some embodiments, the RTase and other RT reagents are added to the sample only after DNase I inactivation. Briefly, add RT buffer and RTase to the whole sample or to an aliquot of the sample and incubate at 42° C. for 30 minutes, followed by heating at 85° C. for 5 minutes to inactivate the RTase. Following RT, place the sample on ice.

Exemplary Reaction Mix and Reaction Protocol for Using a Heat-Labile Hyperactive DNase I with a Thermal-Stable Reverse Transcriptase:

Add DNase MT buffer reagent and DNase I/thermostable RTase to the sample followed by incubation for 5 minutes or more at room temperature or 37° C. for gDNA removal. Inactivate DNase I by heating at 55° C. for 10 min. Continue with the reverse transcription by incubating the sample at 60° C., followed by heating at 85° C. or higher for 10 minutes to inactivate the thermostable RTase. Following RT, place the sample on ice.

Example 2

Generation and Assaying of Activity of Various DNase Mutants

Generation of K- and KS-DNase Mutants:

De Novo gene synthesis approach was used to generate an equine DNase mutant gene having two hyperactive mutations (R13, K74) and one heat-labile mutation (L130) (SEQ ID NO:19). This mutant was called the "K-DNase mutant". The K-DNase mutant was subcloned into pPAL7, a bacterial expression vector (Bio-Rad Laboratories) using Xho I and Hind III restriction enzymes. To introduce a second heat-labile mutation, namely, S-205 insertion, QuickChange mutagenesis approach was used. Briefly, the codon for serine was introduced into the K-mutant by polymerase chain reaction (PCR) using 5'-GACACCACAGTATCAAAATCGACT-CATTG-3' (SEQ ID NO:23) as the forward primer and 5'-CAATGAGTCGATTTTGATACTGTGGTGTC-3' (SEQ ID NO:24) as the reverse primer. A step-up PCR cycling protocol was used and consisted of initial denaturation at 98°

C. for 3 minutes. This was followed by a 5-cycle amplification using denaturation at 98° C. for 30 seconds, primer annealing at 32° C. for 30 seconds and extension at 72° C. for 3 minutes and 25 seconds. Final step involved PCR amplification for 35 cycles using denaturation at 98° C. for 30 seconds, primer annealing at 55° C. for 20 seconds and extension at 72° C. for 3 minutes and 25 seconds. The final extension was done at 72° C. for 5 minutes.

The PCR product was directly used to transform E. coli TOP10 electrocompetent cells. The transformed cells were plated onto an LB-agar plate containing 50 µg/ml of carbenicillin for growth at 37° C. Several colonies were selected for obtaining purified plasmid and S-205 insertion was verified by sequencing. This mutant with the S-205 insertion was called the KS-DNase mutant (SEQ ID NO:18). Therefore, both K- and KS-DNase mutants have the same two "hyperactive" mutations. However, the K-mutant has only one "heat-labile" mutation (L130) and the KS mutant has two "heat-labile" mutations (L130 and S205 insertion).

The K- and KS-DNase mutants were subcloned into pET-29b(+), a bacterial expression vector (EMD Chemicals, Inc.) using Nde I and Xho I restriction enzymes. Two versions of both mutants were generated, one with a carboxyl-terminal His-tag and one with no tag (untagged), and subcloned into pET-29b(+). The His-tagged version was generated for ease of purification of the protein. For untagged version of the mutants, Nde I and Xho I restriction sites were introduced at the 5' and 3' ends respectively of the two mutant genes by PCR using 5'-AGGAGATATACATATGGGTACCCTTCGC-3' (SEQ ID NO:25) as the forward primer and 5'-GTTAAT-TAAGCCTCGAGTTAACCGG-3' (SEQ ID NO:26) as the reverse primer. For the His-tagged version, 5"-AG-GAGATATACATATGGGTACCCTTCGCATTGCCGC-3' (SEQ ID NO:27) was used as the forward primer and 5"-GTGGTGGTGCTCGAGGGGTCCCTGAAAG AGGACTTCAAGACCGGTCATTAAGGTTAC-3' (SEQ ID NO:28) was used as the reverse primer. The His-tag thus generated is removable as the reverse primer contains the sequence for the HRV-3C protease cleavage site (LEV-LFQGP; SEQ ID NO:29) and the tag can be easily removed using HRV-3C protease enzyme. The PCR cycling conditions for generating untagged mutants consisted of initial denaturation at 98° C. for 3 minutes. This was followed by a 35-cycle amplification using denaturation at 98° C. for 30 seconds, primer annealing at 52° C. for 30 seconds and extension at 72° C. for 30 seconds. The final extension was done at 72° C. for 5 minutes. The PCR cycling condition for His-tagged version of the two mutants involved an initial denaturation at 98° C. for 3 minutes. This was followed by a 5-cycle amplification using denaturation at 98° C. for 30 seconds, primer annealing at 42° C. for 30 seconds and extension at 72° C. 30 seconds. Final step involved PCR amplification for 35 cycles using denaturation at 98° C. for 30 seconds, primer annealing at 60° C. for 30 seconds and extension at 72° C. for 30 seconds. The final extension was done at 72° C. for 5 minutes.

The PCR products were purified and digested with Nde I and Xho I restriction enzymes and ligated into pET-29b(+) vector digested with the above two enzymes using T4 DNA ligase per manufacturer's instructions (Life Technologies Corporation). The ligated product was transformed into E. coli Top10 electrocompetent cells. The transformed cells were plated onto an LB-agar plate containing 50 µg/ml of kanamycin for growth at 37° C. Plasmid was purified from several colonies and verified by sequencing.

Expression of K- and KS-DNase Mutants:

K- and KS-DNase mutants in pET-29b(+) were transformed into E. coli BL21 (DE3) cells. The transformed cells were grown at 37° C. by plating them on an LB-agar plate supplemented with 50 µg/ml of kanamycin. Following overnight growth, 3-4 colonies were used to inoculate 10 ml of 2X-YT media supplemented with 50 µg/ml of kanamycin. The cells were grown in a shaker incubator at 37° C. at a constant rotation speed of 275 rpm. When the absorbance of the culture reached 0.6, 1 mM of isopropyl O-D-1-thiogalactopyranoside (IPTG) was added to induce the expression of DNase mutant proteins. An aliquot (1 ml) of culture was collected just prior to induction (0 hour) and at 1 hour and 3 hours post-induction. No significant cell lysis was observed even after 3 hours of induction with IPTG. Cells were harvested after each time point.

The cell pellet was resuspended in 300 µl of lysis buffer containing 10 mM Tris pH 7.6, 2 mM CaCl2, 100 µM PMSF and 100 µM Leupeptin, followed by lysis by sonication at 4° C. using Branson Sonifier 450. The lysate was then centrifuged at 16,000×g for 5 minutes at 4° C. The supernatant was collected and constituted the soluble fraction. The pellet was washed twice with the lysis buffer and then resuspended thoroughly in 300 µl of lysis buffer containing 4M urea, followed by centrifugation at 16,000×g for 5 minutes at 4° C. The supernatant constituted the insoluble fraction. An aliquot (50 µl) of both soluble and insoluble fractions was mixed with 50 µl of Laemmli buffer supplemented with β-mercaptoethanol. The samples were heated in a boiling water bath for 5 minutes, cooled to room temperature and centrifuged.

Expression of the protein in each sample was analyzed by sodium dodecyl sulfate polyacrylamide gel electrophoresis (SDS-PAGE). Briefly, 15 µl of each sample was loaded onto a pre-cast 12% Tris-HCl gel (Bio-Rad Laboratories). The proteins were separated using a constant voltage of 200 V and were visualized by coomasie staining. Expression analysis indicated that both K- and KS-DNase mutants were expressed in very high levels in the cell. However, both mutants were expressed completely in the form of insoluble inclusion body and constituted about 85-90% of the total insoluble fraction (FIG. 2).

Refolding of K- and Ks-DNase Mutants from Inclusion Body and Evaluation of Enzyme Activity of Folded DNase Mutants:

Since the two DNase mutant proteins were expressed in the form of insoluble inclusion body, we isolated, solubilized and folded the mutant proteins from inclusion body using iFOLD® Protein Refolding System-2, iFOLD®-2 (EMD Chemicals, Inc., USA). iFOLD®-2 provides high throughput screening of protein folding conditions as it has 95 unique conditions for protein folding. The refolding process involves five main steps. (1) Isolation and purification of inclusion body; (2) denaturation of inclusion body using iFOLD® guanidine denaturation buffer which has 7 M guanidinium hydrochloride; (3) refolding of protein by rapid dilution into the iFOLD®-2 matrix; (4) evaluation of refolding by assessing the solubility of the protein using absorbance at 340 nm, A340 (the closer the A340 value is to that of water, the more soluble the protein is); and (5) evaluation of activity of folded/soluble protein.

Briefly, 5 g of cell pellet from BL21 (DE3) cells transformed with DNase mutant was used to isolate and purify inclusion body containing His-tagged K- and KS-DNase mutants. The purified inclusion bodies were denatured using the guanidine denaturation buffer supplemented with 10 mM CaCl2 as calcium is critical for structural integrity of DNase I. The denatured inclusion body was then rapidly diluted into the iFOLD®-2 matrix, followed by overnight incubation at room temperature with constant gentle mixing. The A340 values of the samples were measured. A340 value of water (blank) was subtracted from that of the various fractions. Fractions that had blank-subtracted A340 values less than 0.07 were selected and dialyzed against a buffer containing 20 mM HEPES, pH 7.5, 10 mM CaCl2, 10 mM MgCl2 and 1 mM DTT. The dialyzed fractions were concentrated about 4 fold using YM-10 Amicon filters, and the concentrated fractions were evaluated for DNase activity.

Figure 3:
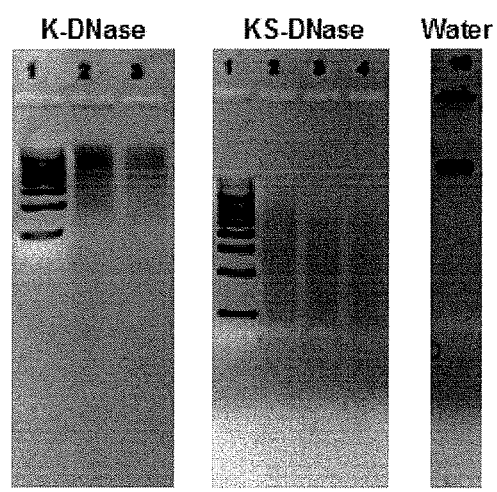
FIG. 3: This figure shows DNase enzyme activity in selected re-folded fractions of His-tagged K- and KS-DNase mutants using the iFOLD® Protein Refolding System-2. DNA digestion using blank fraction (water) was used as a control. Lanes labeled "1" on the gel represent 500 bp DNA ladder.

Evaluation of DNase enzyme activity: Briefly, 20 µl aliquot of folded enzyme fractions was incubated with 300 µg of mouse genomic DNA in presence of DNase reaction buffer for 3 hours at 25° C. The ability of the folded mutant DNase fractions to digest mouse genomic DNA was evaluated by running the reaction mixture on a 1% agarose gel containing ethidium bromide. Several folded fractions of both K- and KS-mutant DNases degraded mouse genomic DNA demonstrating that both K- and KS-mutant DNases were active DNase enzymes (FIG. 3). Western blotting on these fractions using anti-His antibody indicated the presence of His-tagged K- and KS-DNase mutants in these fractions (data not shown).

Figure 4:
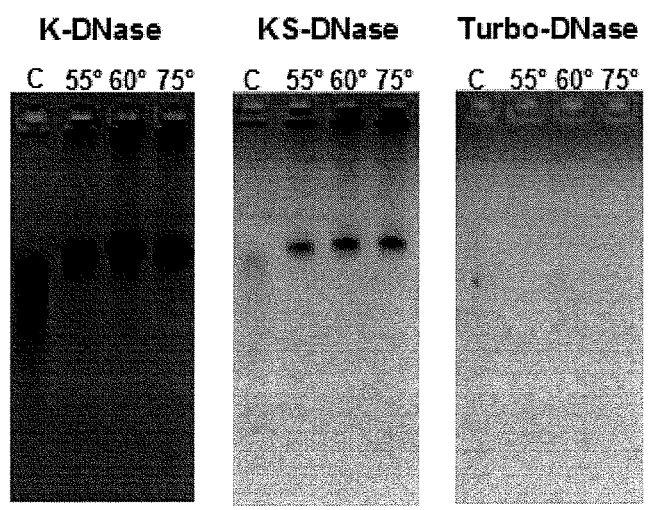
FIG. 4: This figure shows qualitatively the inactivation of His-tagged K- and KS-DNase mutants and Turbo DNase at various temperatures (in ° C.). "C" represents unheated enzyme control.

Evaluation of Thermo-Labile Property of Folded DNase Mutants:

Soluble fractions of both K- and KS-DNase mutants that had DNase activity were heated for 10 minutes at 55° C., 60° C. and 75° C. The ability of these heated fractions to digest mouse genomic DNA was evaluated and compared against that of corresponding "unheated" fraction. Turbo DNase, a hyperactive bovine DNase (Life Technologies Corporation) was used as a control to compare the heat-labile property of K- and KS-mutant DNases with that of Turbo DNase. The extent of digestion was evaluated qualitatively by gel analysis using 1% agarose gel containing ethidium bromide. Results indicated that both K- and KS-DNase mutants were significantly inactivated by heating at 60° C., whereas the Turbo DNase was not inactivated even at 75° C. (FIG. 4). These qualitative results suggest that both K- and KS-DNase mutants are relatively thermo-labile as compared to a hyperactive bovine DNase.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated DNase I polypeptide having an amino acid sequence comprising SEQ ID NO:18 or SEQ ID NO:19.

2. The isolated DNase I polypeptide of claim 1, wherein the DNase comprises SEQ ID NO:19.

3. The isolated DNase I polypeptide of claim 1, wherein the DNase comprises SEQ ID NO:18.

4. The isolated DNase I polypeptide of claim 1, wherein the polypeptide further comprises a heterologous sequence-non-specific double-stranded DNA binding domain.

5. The isolated DNase I polypeptide of claim 4, wherein the DNA binding domain is selected from the group consisting of a DNA binding domain from a Maf proto-oncogene transcription factor, an Sso family DNA binding protein and a HMf transcription factor.

6. A method for removing DNA from a sample, the method comprising,
   incubating the sample with the DNase I polypeptide of claim 1, wherein the incubating step is performed under conditions sufficient to degrade at least a majority of the DNA in the sample.

7. The method of claim 6, further comprising heating the sample thereby substantially eliminating the DNase activity of the polypeptide.

8. The method of claim 6, further comprising following the heating step performing a reverse transcription reaction on RNA present in the sample.

9. A synthetic or isolated nucleic acid comprising a polynucleotide encoding the DNase I polypeptide of claim 1.

10. The synthetic or isolated nucleic acid of claim 9, wherein the DNase I polypeptide comprises SEQ ID NO:19.

\* \* \* \* \*